(12) United States Patent
Kazerooni et al.

(10) Patent No.: US 7,947,004 B2
(45) Date of Patent: May 24, 2011

(54) LOWER EXTREMITY EXOSKELETON

(75) Inventors: Homayoon Kazerooni, Berkeley, CA (US); Nathan H. Harding, Oakland, CA (US); Russdon Angold, American Canyon, CA (US)

(73) Assignee: The Regents of the University of California, Oakland, CA (US)

( * ) Notice: Subject to any disclaimer, the term of this patent is extended or adjusted under 35 U.S.C. 154(b) by 1307 days.

(21) Appl. No.: 11/335,392

(22) Filed: Jan. 18, 2006

(65) Prior Publication Data

US 2006/0260620 A1 Nov. 23, 2006

Related U.S. Application Data

(60) Provisional application No. 60/645,417, filed on Jan. 18, 2005.

(51) Int. Cl.
*A61F 5/00* (2006.01)

(52) U.S. Cl. ............. 602/16; 602/23; 602/26; 602/27

(58) Field of Classification Search ............ 602/16, 602/19, 5, 23, 26–27; 482/51; 128/882
See application file for complete search history.

(56) References Cited

U.S. PATENT DOCUMENTS

| | | |
|---|---|---|
| 406,328 A | 7/1889 | Yagn |
| 420,178 A | 1/1890 | Yagn |
| 420,179 A | 1/1890 | Yagn |
| 440,684 A | 11/1890 | Yagn |
| 539,872 A | 5/1895 | Kheiralla |
| 807,908 A | 12/1905 | Bradstreet |
| 979,243 A | 12/1910 | Anderson |
| 1,308,675 A | 7/1919 | Kelley |
| 4,647,004 A * | 3/1987 | Bihlmaier ............... 251/28 |
| 4,964,628 A * | 10/1990 | Poplawski ............... 482/51 |
| 5,020,790 A * | 6/1991 | Beard et al. ............ 482/4 |
| 5,282,460 A | 2/1994 | Boldt |

(Continued)

FOREIGN PATENT DOCUMENTS

CN 1586434 A 3/2005

(Continued)

OTHER PUBLICATIONS

International Search Report and Written Opinion mailed Jan. 28, 2008, for PCT Application No. PCT/US07/06122 filed Mar. 9, 2007, 12 pages.

(Continued)

*Primary Examiner* — Michael A. Brown
(74) *Attorney, Agent, or Firm* — Diederiks & Whitelaw, PLC

(57) ABSTRACT

A lower extremity exoskeleton, configurable to be coupled to a person, comprises two leg supports configurable to be coupled to the person's lower limbs and configured to rest on the ground during their stance phases. Each leg support comprises a thigh link, a shank link, and two knee joints. Each knee joint is configured to allow flexion and extension between the respective shank link and the respective thigh link. The lower extremity exoskeleton also comprises an exoskeleton trunk configurable to be coupled to the person's upper body. The exoskeleton trunk is rotatably connectable to the thigh links of the leg supports allowing for the flexion and extension between the leg supports and the exoskeleton trunk. In this exemplary embodiment, the energy required for flexion and extension movement between the shank link and the respective thigh link of a leg support over a cyclic knee motion is provided by the person.

84 Claims, 28 Drawing Sheets

U.S. PATENT DOCUMENTS

| | | | | |
|---|---|---|---|---|
| 5,476,441 | A | * 12/1995 | Durfee et al. | 602/23 |
| 5,658,242 | A | 8/1997 | McKay et al. | |
| 5,662,693 | A | * 9/1997 | Johnson et al. | 607/49 |
| 5,961,476 | A | 10/1999 | Betto et al. | |
| 6,422,329 | B1 | 7/2002 | Kazerooni et al. | |
| 6,500,210 | B1 | 12/2002 | Sabolich et al. | |
| 6,676,707 | B2 | 1/2004 | Yih et al. | |
| 6,807,869 | B2 | 10/2004 | Farringdon et al. | |
| 6,821,233 | B1 | * 11/2004 | Colombo et al. | 482/54 |
| 6,966,882 | B2 | 11/2005 | Horst | |
| 7,041,074 | B1 | * 5/2006 | Averianov et al. | 602/20 |
| 7,048,707 | B2 | 5/2006 | Schwenn et al. | |
| 7,111,704 | B2 | 9/2006 | Johnson | |
| 7,153,242 | B2 | 12/2006 | Goffer | |
| 7,393,335 | B2 | * 7/2008 | Carvey et al. | 602/26 |
| 2004/0024340 | A1 | * 2/2004 | Schwenn et al. | 602/62 |
| 2004/0116839 | A1 | * 6/2004 | Sarkodie-Gyan | 601/35 |
| 2006/0046907 | A1 | 3/2006 | Rastegar et al. | |
| 2007/0233279 | A1 | 10/2007 | Kazerooni et al. | |
| 2008/0154165 | A1 | 6/2008 | Ashihara et al. | |

FOREIGN PATENT DOCUMENTS

CN            101094640 A     12/2007

OTHER PUBLICATIONS

Johnson, D., et al. "Development of a Mobility Assist for the Paralyzed, Amputee, and Spastic Patient." Proceedings of the Fifteenth Southern Biomedical Engineering Conference, IEEE, pp. 67-70, Dayton, Ohio, Mar. 1996.

Yamamoto, K., et al. "Development of Power Assisting Suit for Assisting Nurse Labor." JSME International Journal Series C., vol. 45, No. 3, Sep. 2002.

Yamamoto, K., et al. "Development of Power Assisting Suit (Miniaturization of Supply System to Realize Wearable Suit)." JSME International Journal Series C., vol. 46, No. 3, Sep. 2003.

Vukobratovic, M., et al. "Development of Active Anthropomorphic Exoskeletons." Medical and Biological Engineering, pp. 66-80, Jan. 1974.

Misuraca, J., et al. "Lower Limb Human Muscle Enhancer." Proceedings of the Symposium on Advances in Robot Dynamics and Control, ASME International Mechanical Engineering Congress and Exposition (IMECE), New York, New York, Nov. 2001.

Belforte, G., et al. "Pneumatic Active Gait Orthosis." Mechatronics, vol. 11, No. 3, pp. 301-323, Apr. 2001.

Kasaoka, K., et al. "Predictive Control Estimating Operator's Intention for Stepping-up Motion by Exoskeleton Type Power Assist System HAL." Proceedings of the IEEE/RJS International Conference on Intelligent Robots and Systems (IROS), vol. 3, pp. 1578-1583, Maui, Hawaii, Nov. 2001.

Kawamoto, H., et al. "Comfortable Power Assist Control Method for Walking Aid by HAL-3." Proceedings of the IEEE International Conference on Systems, man, and Cybernetics (SMC), vol. 4, Hammamet, Tunisia, Oct. 2002.

Lee, S. et al. "Power Assist Control for Walking Aid with HAL-3 Based on EMG and Impedance Adjustment around Knee Joint." Proceedings of the IEEE/RJS International Conference on Intelligent Robots and Systems (IROS), vol. 2, pp. 1499-1504, Lausanne, Switzerland, 2002.

Kawamoto, H., et al. "Power Assist System HAL-3 for Gait Disorder Person." Lecture Notes in Computer Science (LNCS), vol. 2398, Proceedings of the Eighth International conference on Computers Helping People with Special Needs (ICCHP), pp. 196-203, Berlin, Germany, 2002.

Van Den Bogert, A. "Exotendons for Assistance of Human Locomotion." Biomedical Engineering Online, vol. 2, Oct. 2003.

Mori, Y., et al. "Development of Straight Style Transfer Equipment for Lower Limbs Disabled." Proceedings of the IEEE International Conference on Robotics and Automation (ICRA), vol. 3, pp. 2486-2491, New Orleans, Louisiana, May 2004.

Irby, S., et al. "Automatic Control Design for a Dynamic Knee-Brace System." IEEE Transactions on Rehabilitation Engineering, vol. 7, No. 2, pp. 135-139, Jun. 1999.

Ferris, D., et al. "An Ankle-foot Orthosis Powered by Artificial Muscles." Proceedings of the 25th Annual Meeting of the American Society of Biomechanics, San Diego, California, Aug. 2001.

Naruse, K., et al. "Design of Compact and Lightweight Wearable Power Assist Device." Proceedings of ASME International Mechanical Engineering Congress and Exposition (IMECE), Washington D.C., Nov. 2003.

Pratt, J., et al. "The RoboKnee: An Exoskeleton for Enhancing Strength and Endurance During Walking." Proceedings of the IEEE International Conference on robotics and Automation (ICRA), vol. 3, pp. 2430-2435; New Orleans, Louisiana, May 2004.

Morris, S., et al. "Shoe-integrated Sensor System for Wireless Gait Analysis and Real-Time Feedback." Proceedings of the Second Joint EMBS/BMES Conference, pp. 2468-2469, Houston Texas, Oct. 2002.

Harley, J.A. "Design and Construction of an Underactuated Assistive Walking Device." Graduate Thesis, UC-Berkeley Mechanical Engineering Dept., Aug. 1995.

Lim, Michael Zin Min, "An Analysis on the Performance of an Underactuated Lower Extremity Enhancer." Graduate Thesis, UC-Berkeley Mechanical Engineering Dept., 2000.

Clark, D.C. et al. "Exploratory Investigation of the Man Amplifier Concept." Technical Documentary Report No. AMRL-TDR-62-89, United States Air Force, Wright-Patterson Air. Force Base, Ohio, Aug. 1962.

"Machine Augmentation of Human Strength and Endurance: Hardiman I Prototype Project." General Electric Company, Schenectady, New York, Jul. 1969.

Makinson, B.J. "Research and Development Prototype for Machine Augmentation of Human Strength and Endurance: Hardiman I Project." General Electric Company, Schenectady, New York, May 1971.

Gilbert, K.E. "Exoskeleton Prototype Project." General Electric Company, Schenectady, New York, Oct. 1966.

Mosher, R.S. "Handyman to Hardiman." Automotive Engineering Congress, Society of Automotive Engineers, Detroit, Michigan, Jan. 1967.

Arroyo, P. "Design of a Minimally Actuated Assistive Device." Graduate Thesis, UC-Berkeley Mechanical Engineering Dept., 1998.

Rehnmark, F.L. "Dynamic Simulation and Design of a Powered Underactuated Assistive Walking Device." Graduate Thesis, UC-Berkeley Mechanical Engineering Dept., 1997.

Chu, A. "Design Overview of $1^{st}$ Generation Exoskeleton," Master of Science Thesis, UC Berkeley, Apr. 3, 2003.

Zoss, A. "Mechanical Design Implementation of an Exoskeleton," Master of Science Thesis, UC Berkeley, Spring 2003.

U.S. Appl. No. 10/976,652, filed Oct. 29, 2004, for Kazerooni.

U.S. Appl. No. 11/404,719, filed Apr. 13, 2006, for Kazerooni.

Racine, J.C. (2003). "Control of a Lower Exoskeleton for Human Performance Amplification," PhD Thesis, UC Berkeley, pp. 1-340.

International Search Report and Written Opinion mailed Aug. 15, 2007, for PCT Application No. PCT/US06/14227 filed Apr. 13, 2006, 13 pages.

International Search Report and Written Opinion mailed Aug. 7, 2007, for PCT Application No. PCT/US06/01981 filed Jan. 18, 2006, 11 pages.

* cited by examiner

LOWER EXTREMITY EXOSKELETON

CROSS-REFERENCE TO RELATED APPLICATIONS

This application claims the benefit of U.S. Provisional Application No. 60/645,417, titled LOWER EXTREMITY EXOSKELETON, filed Jan. 18, 2005, the entire content of which is incorporated herein by reference.

STATEMENT REGARDING FEDERALLY SPONSORED RESEARCH OR DEVELOPMENT

This invention was made with government support under Contract No. DAAD19-01-1-0509 awarded by Defense Advanced Research Projects Agency (DARPA). The government has certain rights in the invention.

BACKGROUND

1. Field

The present application relates generally to the field of lower extremity exoskeletons and more specifically to the field of low power lower extremity exoskeletons.

2. Related Art

In a wide variety of situations, people are often frustrated in attempting to carry excessively heavy or bulky objects while walking. Some people cannot even carry their own weights without becoming tired quickly or injured. Opportunities exist, therefore, to provide a compact, easy-to-operate, fast, and general purpose device to carry loads and weights while the device is coupled to a person.

SUMMARY

In one exemplary embodiment, a lower extremity exoskeleton is configurable to be coupled to a person. The lower extremity exoskeleton comprises two leg supports configurable to be coupled to the person's lower limbs and configured to rest on the ground during their stance phases. Each leg support comprises a thigh link, a shank link, and two knee joints. Each knee joint is configured to allow flexion and extension between the respective shank link and the respective thigh link. The lower extremity exoskeleton also comprises an exoskeleton trunk configurable to be coupled to the person's upper body. The exoskeleton trunk is rotatably connectable to the thigh links of the leg supports allowing for the flexion and extension between the leg supports and the exoskeleton trunk. In this exemplary embodiment, the energy required for flexion and extension movement between the shank link and the respective thigh link of a leg support over a cyclic knee motion is provided by the person.

DESCRIPTION OF DRAWING FIGURES

The present application can be best understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
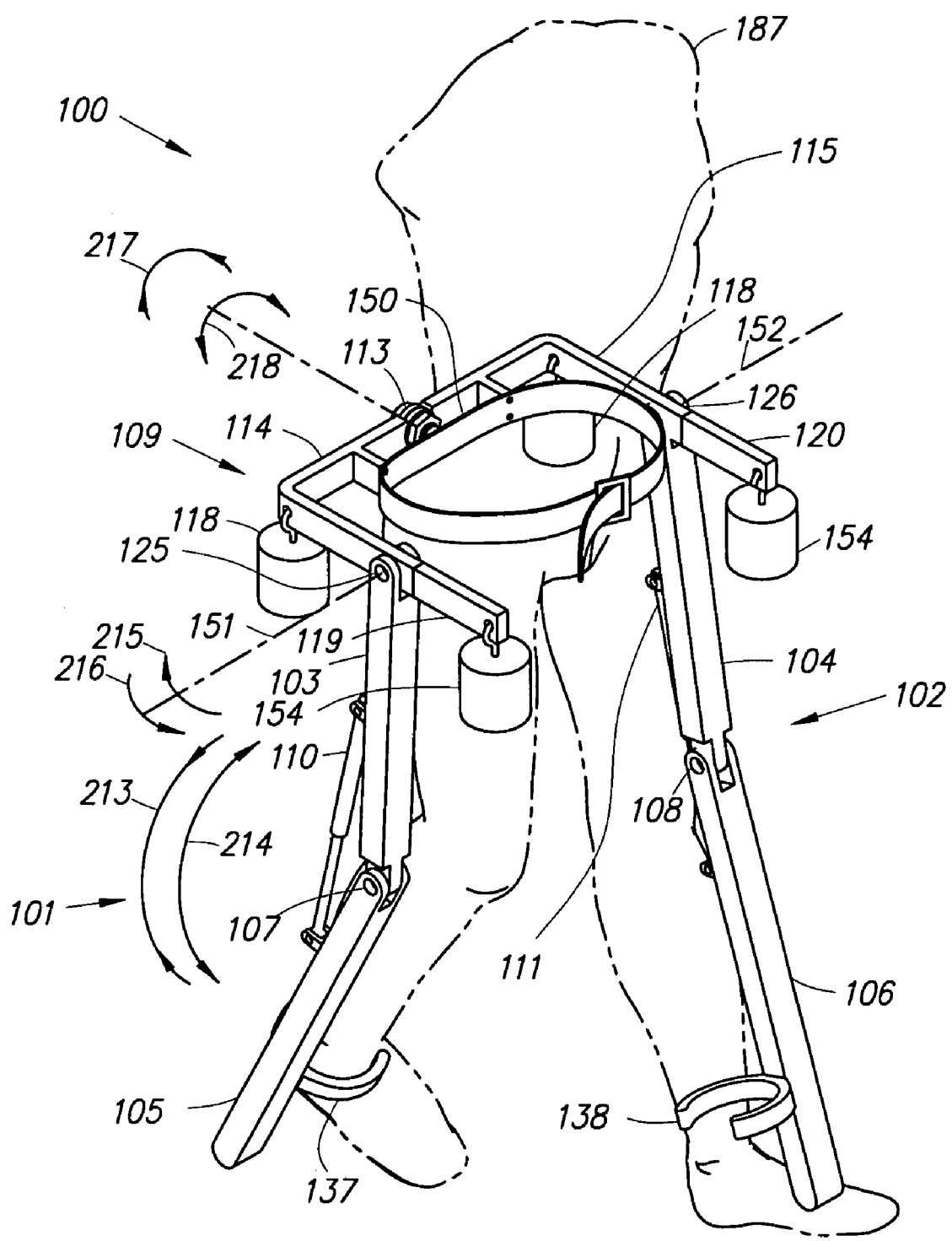
FIG. 1 is a front view perspective drawing in accordance with an embodiment of the present invention.
Figure 2:
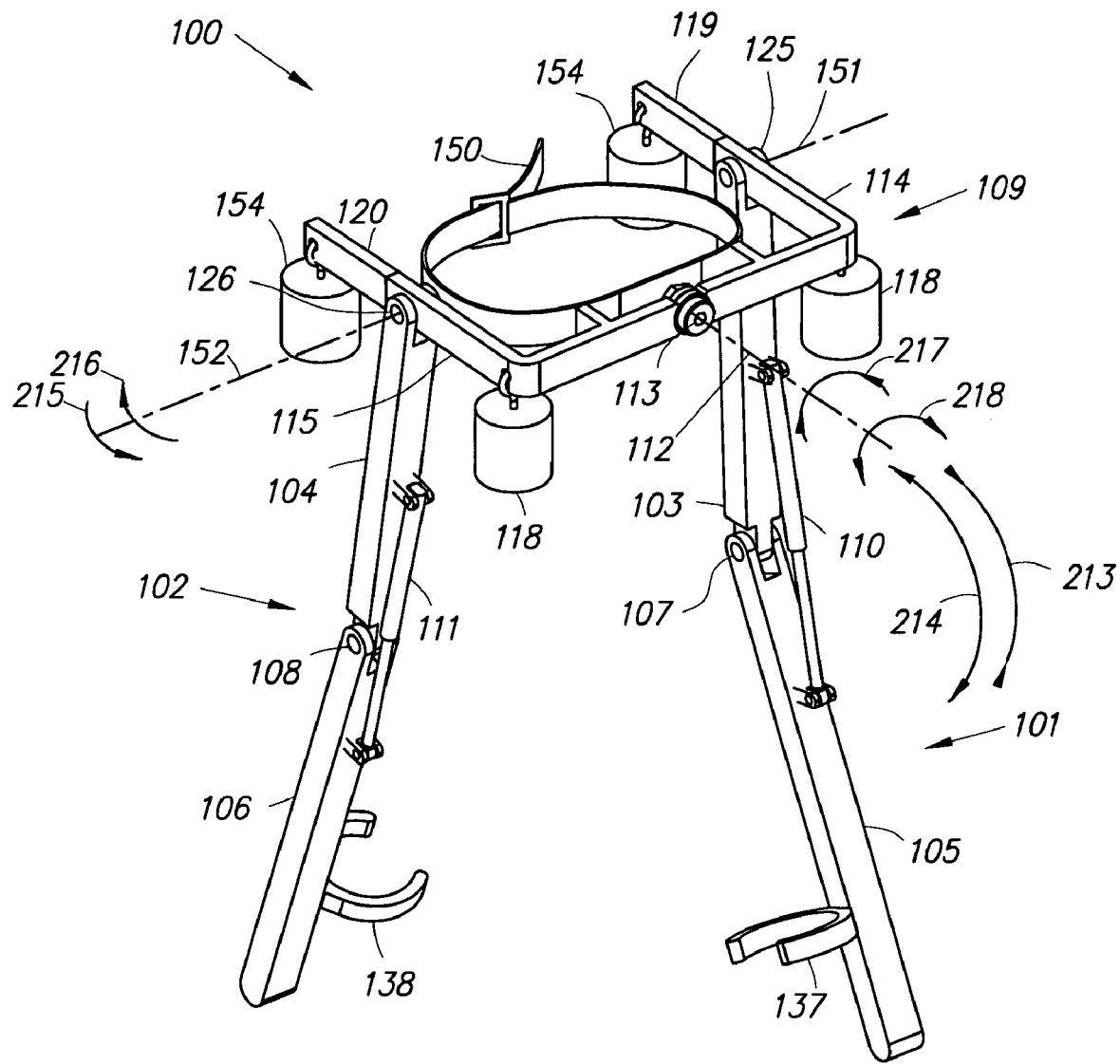
FIG. 2 is a rear view perspective drawing of the embodiment of FIG. 1.

In accordance with an embodiment of the present invention, FIGS. 1 and 2 are front view and rear view perspective drawings illustrating a lower extremity exoskeleton 100. Lower extremity exoskeleton 100 is configurable to be coupled to a person 187. Lower extremity exoskeleton 100 comprises two leg supports 101 and 102 which are configurable to be coupled to the person's lower limbs and configured to rest on the ground during the stance phase of each leg support. The leg supports comprise thigh links 103 and 104 and shank links 105 and 106. Two knee joints 107 and 108 are configured to allow flexion and extension (shown by arrows 213 and 214 respectively) between the shank link and the thigh link of leg supports 101 and 102. Lower extremity exoskeleton 100 further comprises an exoskeleton trunk 109. Exoskeleton trunk 109, among other components, comprises a human interface device 150. Exoskeleton trunk 109 is configurable to be coupled to the person's upper body through human interface device 150. The person's upper body means any location above the thighs. Exoskeleton trunk 109 is rotatably connectable to thigh links 103 and 104 of leg supports 101 and 102 at hip flexion-extension joints 125 and 126, allowing for the hip flexion and extension rotations (shown by arrows 215 and 216 respectively) of leg supports 101 and 102 about hip flexion-extension axes 151 and 152 respectively.

In operation the energy required for flexion and extension movement between a shank link (105 or 106) and the corresponding thigh link (103 and 104) of a leg support over a cyclic knee motion is provided by person 187. A cyclic knee motion here is defined as a motion where the initial and the final configurations of a shank link (105 or 106) and its corresponding thigh link (103 or 104) with respect to each other are nearly identical. In particular when a leg support is in a swing phase, a cyclic knee motion is a motion where the leg support is not in contact with the ground and the initial and the final configurations of the corresponding shank link and thigh link with respect to each other are nearly identical. Likewise, when a leg support is in a stance phase, a cyclic knee motion is a motion where the leg support is in contact with the ground and the initial and the final configurations of the corresponding shank link and thigh link with respect to each other are nearly identical.

In the above embodiment, the torque required for flexion or extension between shank link (105 or 106) and the corresponding thigh link (103 and 104) is provided by person 187. Two knee joints 107 and 108, each configured to allow flexion and extension between respective shank link (105 or 106) and the corresponding thigh link (103 and 104) without the use of energy from a power source other than the energy provided by the person. A power source may be used in lower extremity exoskeleton 100 to provide power for sensors, computers and other components, but does not provide energy for flexion and extension motion between the shank links the thigh links. By power source we mean any system that produces power such as batteries, compressed gas, air compressors, hydraulic compressors, combustion engines, solar cells, and the like.

In some embodiments of the invention, each said leg support is configured to allow flexion of the respective knee joint during the swing phase, and to resist flexion of the respective knee joint during the stance phase to allow the transfer of a force to the ground.

In operation, person 187 couples to (or wears) lower extremity exoskeleton 100 by coupling to human interface device 150 (a simple belt in this case of FIG. 1) and by coupling to two leg supports 101 and 102. In some embodiments as shown in FIG. 1, leg supports 101 and 102 comprise shank holding devices 137 and 138 that couple person 187 to leg supports 101 and 102.

In some embodiments of the invention, the energy required for flexion and extension of thigh links 103 and 104 about hip flexion-extension axes 151 and 152 over a cyclic hip motion is also provided by person 187. A cyclic hip motion here is defined as a motion where the initial and the final configurations of a thigh link (103 or 104) with respect to exoskeleton trunk 109 are nearly identical.

In some embodiments as shown in FIG. 1, exoskeleton trunk 109 includes two hip links 114 and 115 rotatably connectable to thigh links 103 and 104 at hip flexion-extension joints 125 and 126, allowing for the flexion and extension of leg supports 101 and 102 about hip flexion-extension axes 151 and 152 respectively. In some embodiments, hip links 114 and 115 are rotatably connected to each other at abduction-adduction joint 113 allowing for abduction and/or adduction of leg supports 101 and 102. Abduction and adduction of leg supports 101 and 102 are shown by arrows 217 and 218 respectively.

In some embodiments, exoskeleton trunk 109 is configured to hold a rear load 118 behind person 187. In some embodiments, as shown in FIG. 1, rear load 118 is held by hip links 114 and 115. In some embodiments, exoskeleton trunk 109 further comprises extension frames 119 and 120 configured to hold a front load 154 in front of person 187. In some embodiments (as shown in FIG. 1) extension frames 119 and 120 are connectable to hip links 114 and 115. Examples of rear load 118 and front load 154 include without limitation, backpack, baby carrier, food containers, sacks, water jugs, tool boxes, barrels, ammunition, weaponry, bedding, first aid supplies, golf bags, mail bags, camera, leaf blower, compressor, electromechanical machineries and combinations thereof. In some embodiments, rear load 118 and/or front load 154 are another person being carried by person 187. In some embodiments, exoskeleton trunk 109 supports a portion of the weight of person 187 through human interface device 150.

Figure 3:
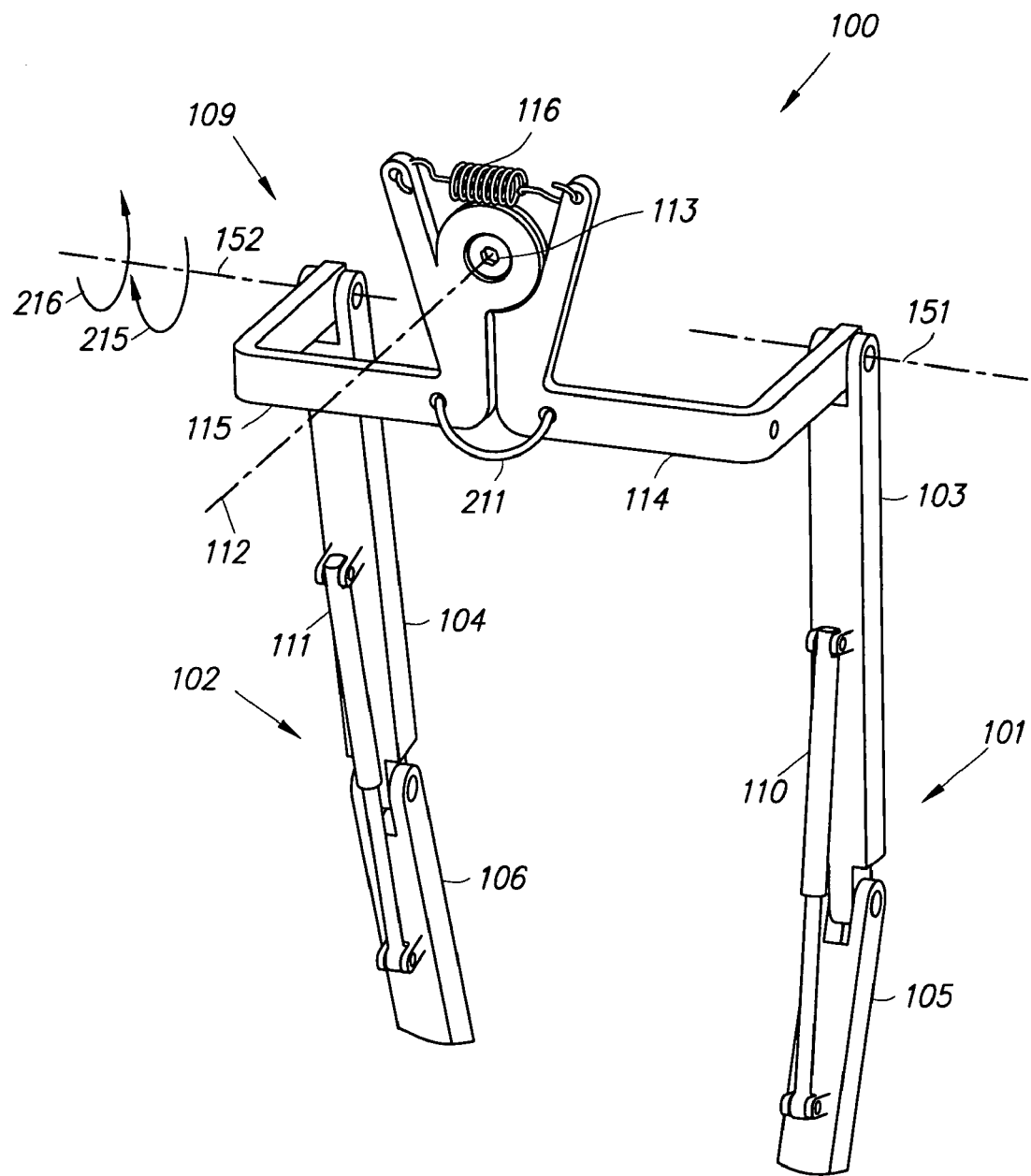
FIG. 3 is a perspective drawing in accordance with an embodiment of the present invention.

In some embodiments of the invention, as shown in FIG. 3, exoskeleton trunk 109 further comprises a hip resilient element 116 configured to apply a torque between hip links 114 and 115. Examples of a hip resilient element include, without limitation, extension spring, compression spring, leaf spring, gas spring, air spring, rubber, elastomer, surgical tube, bungee cord and combinations thereof. The stiffness of hip resilient element 116 may be chosen such that its force generally holds up the weight of the leg supports 101 or 102 during swing phase.

Some embodiments, as shown in FIG. 3, may also include a hip abduction stop 211 which limits the abduction of hip links 114 and 115 with respect to each other. In the particular embodiment shown in FIG. 3, abduction stop 211 is created using a wire rope. Wire rope 211 limits the abduction of leg supports 101 and 102 but allows adduction of leg supports 101 and 102.

Figure 4:
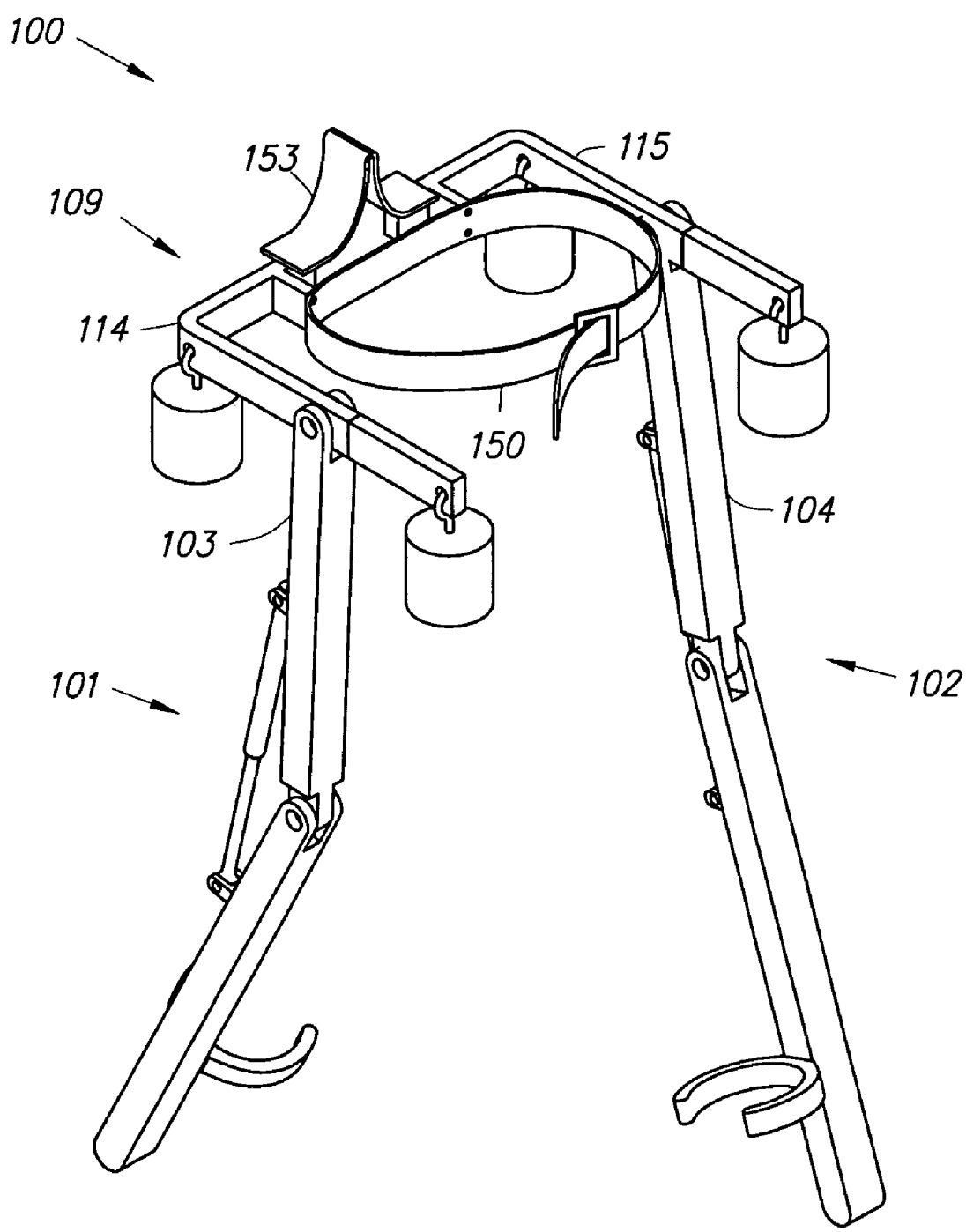
FIG. 4 is a perspective drawing in accordance with an embodiment of the present invention.

In accordance with another embodiment of the invention, FIG. 4 is a perspective drawing where exoskeleton trunk 109 includes two hip links 114 and 115 rotatably connectable to thigh links 103 and 104 allowing for flexion and extension of support legs 101 and 102 relative to exoskeleton trunk 109, wherein hip links 114 and 115 are compliantly connected to each other allowing for abduction and/or adduction of leg supports 101 and 102. In the example shown in FIG. 4, this is accomplished by leaf spring 153.

Figure 5:
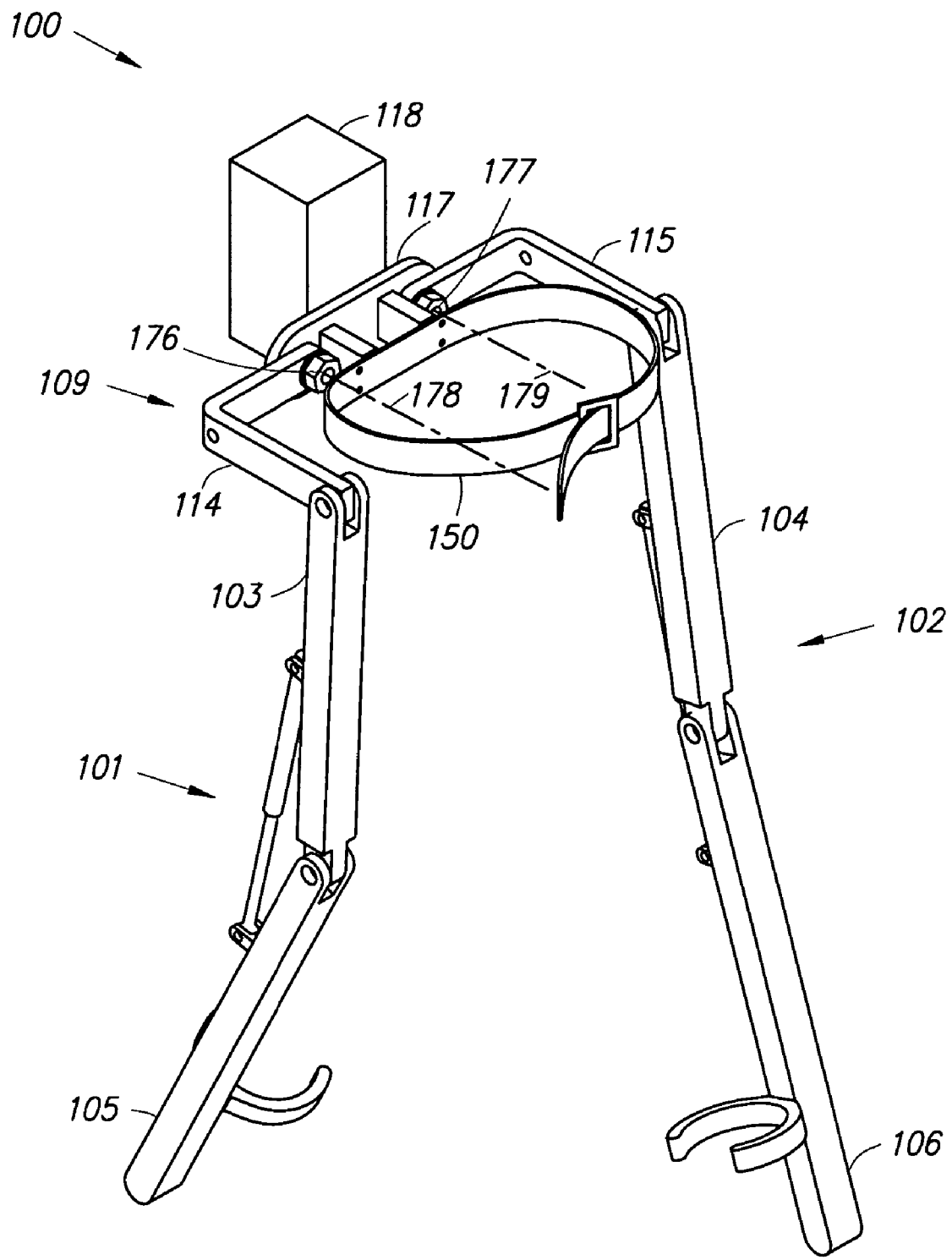
FIG. 5 is a perspective drawing in accordance with an embodiment of the present invention.

In accordance with another embodiment of the invention, FIG. 5 is a perspective drawing wherein exoskeleton trunk 109 further comprises a connecting bracket 117 configured to transfer the weight of rear load 118 to exoskeleton trunk 109. Exoskeleton trunk 109 further comprises two hip links 114 and 115 rotatably connectable to thigh links 103 and 104 allowing for flexion and extension of leg supports 101 and 102 relative to exoskeleton trunk 109. Hip links 114 and 115 are rotatably connected to connecting bracket 117 via two hip abduction-adduction joints 176 and 177 and rotate about two hip abduction-adduction axes 178 and 179. In some embodiments, hip abduction-adduction axes 178 and 179 are generally parallel to each other. In some embodiments, hip abduction-adduction joints 176 and 177 coincide with each other. Furthermore, in some embodiments, as shown in FIG. 6, hip abduction-adduction joints 176 and 177 coincide with each other forming hip abduction-adduction joint 113 and hip abduction-adduction axes 178 and 179 become one hip abduction-adduction axis 112.

Figure 6:
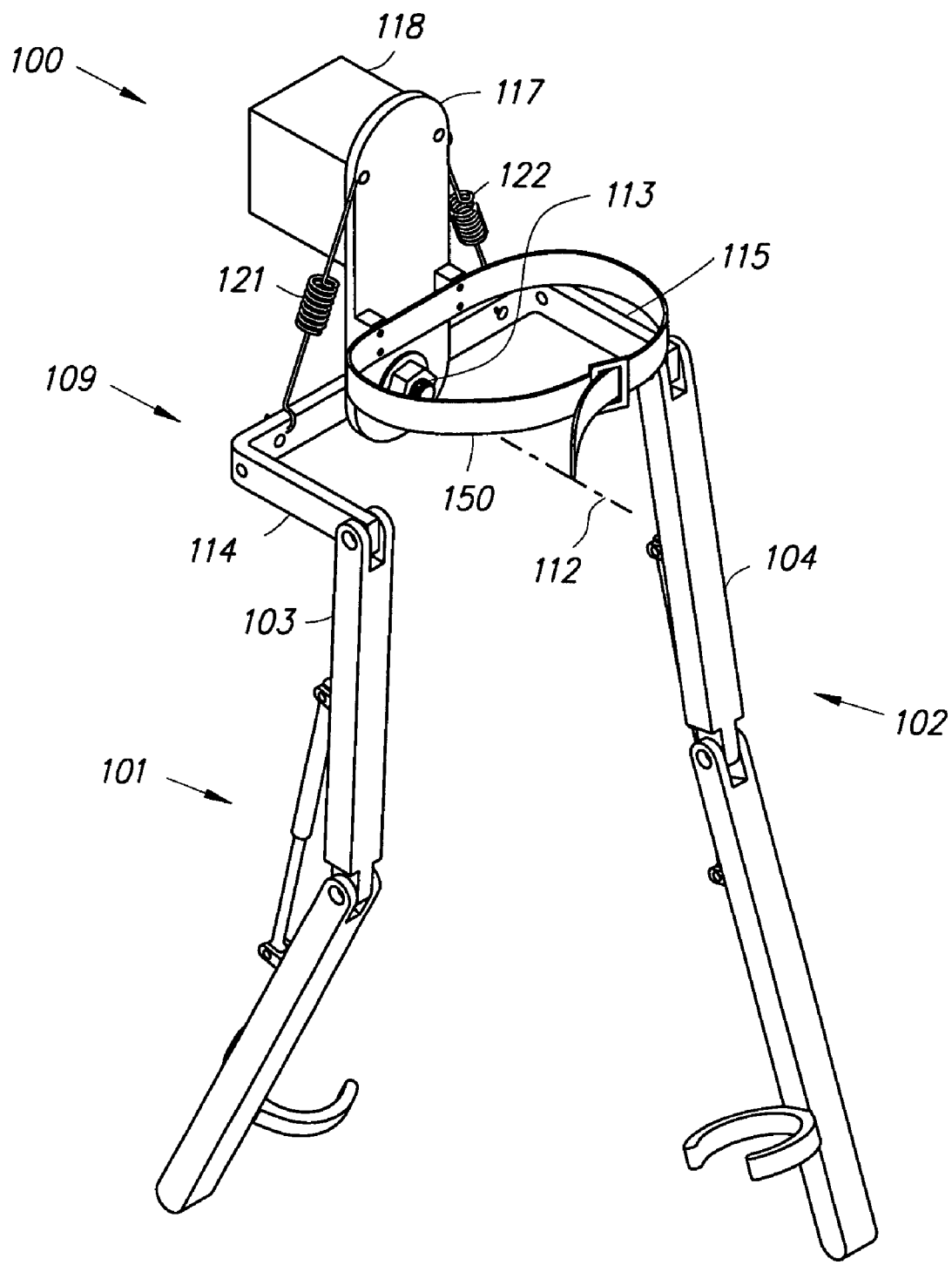
FIG. 6 is a perspective drawing in accordance with an embodiment of the present invention.
Figure 7:
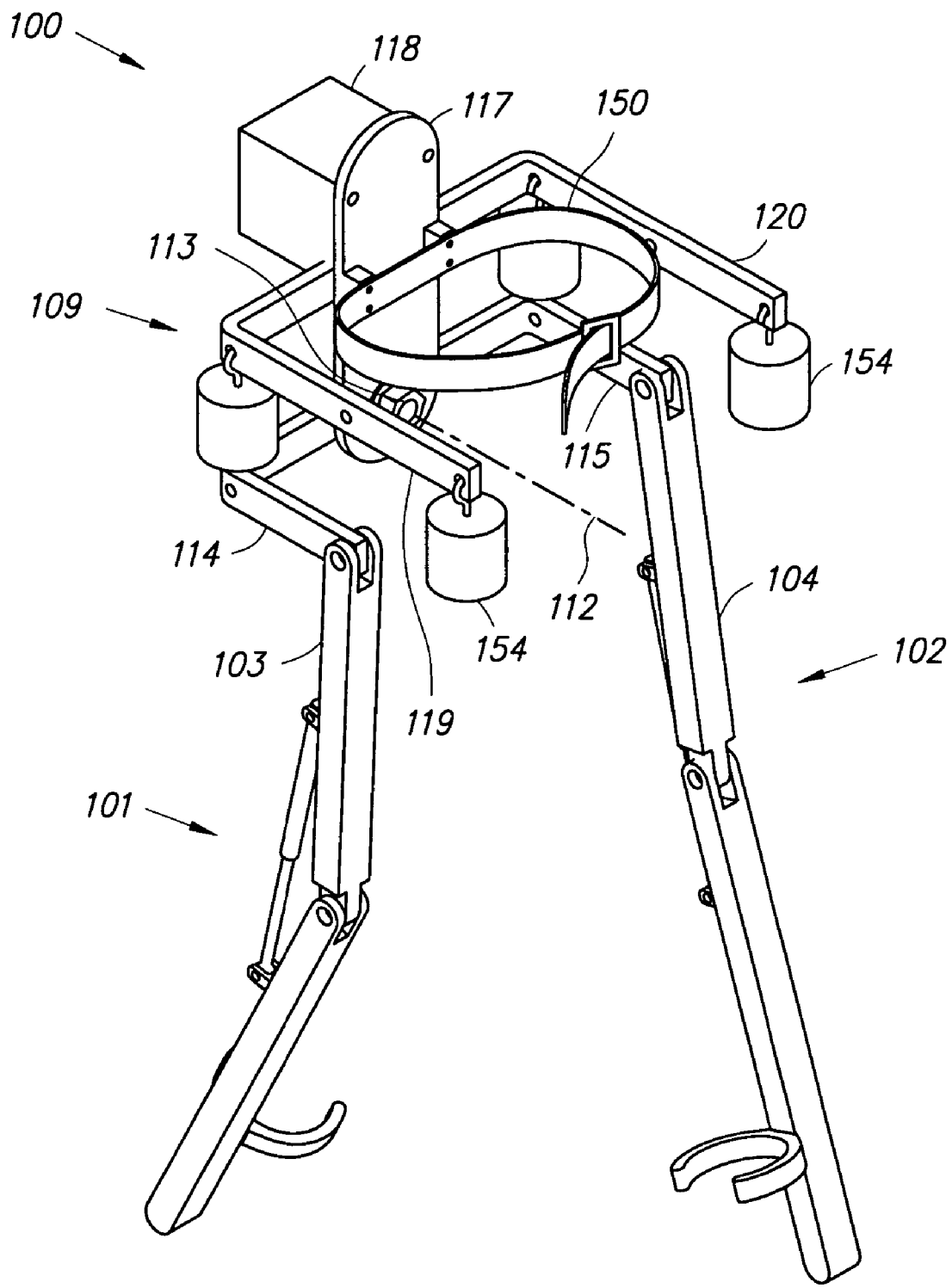
FIG. 7 is a perspective drawing in accordance with an embodiment of the present invention.

In some embodiments, as shown in FIG. 6, exoskeleton trunk 109 further comprises hip abduction-adduction resilient elements 121 and 122 configured to apply torques between hip links 114 and 115 and connecting bracket 117. Examples of hip abduction-adduction resilient elements include, without limitation, extension spring, compression spring, gas spring, air spring, rubber, surgical tube, leaf springs, bungee cord and combinations thereof. The stiffness of hip abduction-adduction resilient elements 121 and 122 may be chosen such that its force generally holds up the weight of the leg supports 101 or 102 during swing phase and aid the person in keeping the load oriented vertically while walking. In some embodiments as shown in FIG. 7, connecting bracket 117 further comprises extension frames 119 and 120 configured to hold front load 154 in front of person 187.

Figure 13:
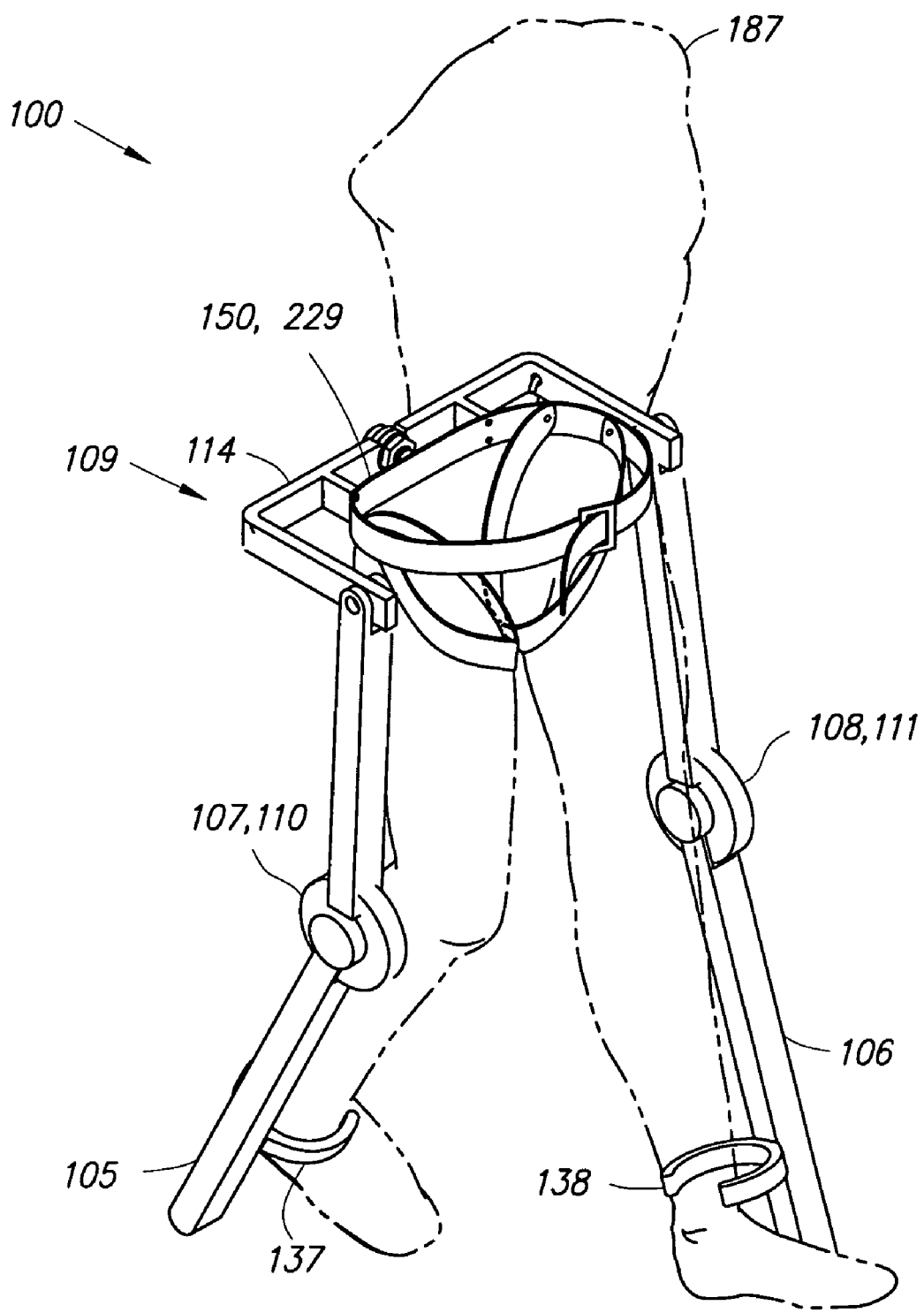
FIG. 13 is a perspective drawing in accordance with an embodiment of the present invention.

In some embodiments of the invention, as shown in FIGS. 1, 5, 6 and 7, exoskeleton trunk 109 comprises human interface device 150 capable of coupling person 187 to lower extremity exoskeleton 100. Examples of human interface device 150 comprise an element or combination of elements including, without limitation, vests, belts, straps, shoulder straps, chest straps, body cast, harness, and waist belts. In some embodiment human interface device 150 transfers a portion of the weight of person 187 to exoskeleton trunk 109. FIG. 13 shows an embodiment of the invention where human interface device 150 comprises a specially-designed harness 229 to fit the body of person 187. Harness 229 transfers a portion of the weight of person 187 to exoskeleton trunk 109.

Figure 8:
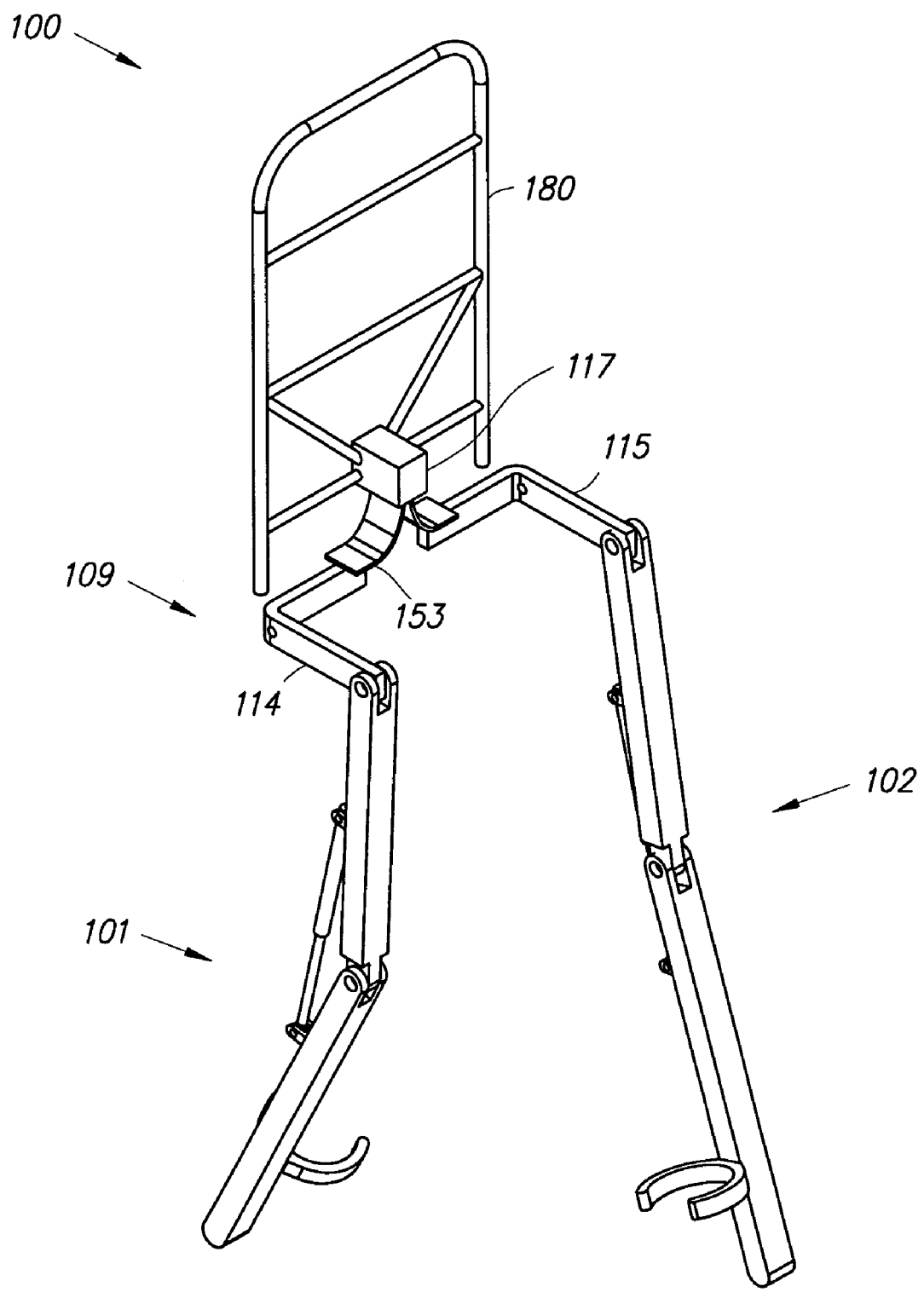
FIG. 8 is a perspective drawing in accordance with an embodiment of the present invention.

In some embodiments, as shown in FIG. 8, hip links 114 and 115 are compliantly connected to connecting bracket 117. In the embodiment shown in FIG. 8, this is accomplished by a hip compliant member 153 which in this case is a leaf spring.

In some embodiments, as shown in FIG. 8, exoskeleton trunk 109 comprises a backpack frame 180 that allows a backpack to be coupled to lower extremity exoskeleton 100. In some embodiments, backpack frame 180 is connected to connecting bracket 117. The human interface devices 150 (such as a belt and shoulder straps) have been omitted in this figure for clarity.

Figure 9:
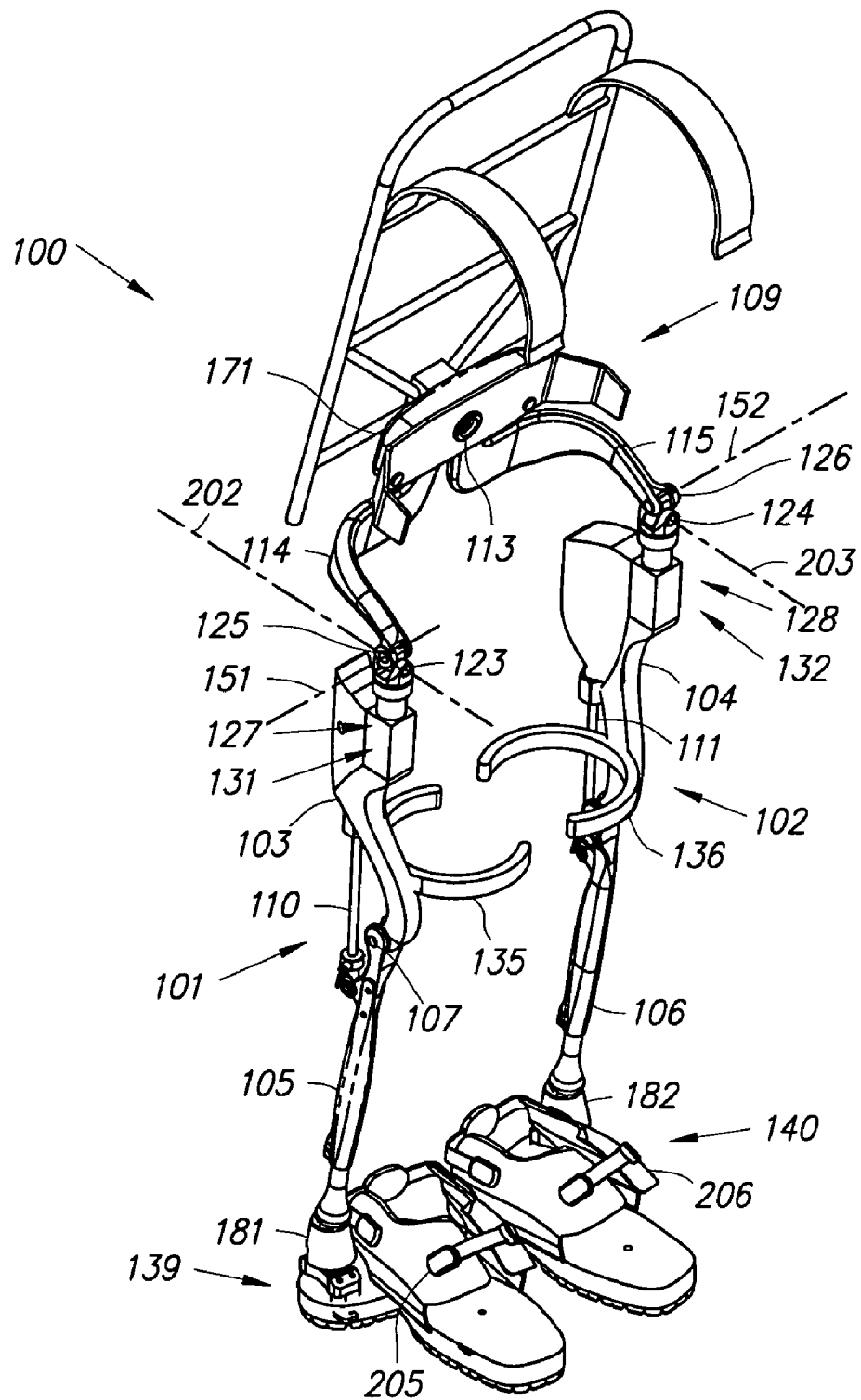
FIG. 9 is a perspective drawing in accordance with an embodiment of the present invention.

In accordance with another embodiment of the invention, FIG. 9 is a perspective drawing wherein leg supports 101 and 102 further include thigh abduction-adduction joints 123 and 124 configured to allow abduction and/or adduction of leg supports 101 and 102 about axes 202 and 203 respectively. In some embodiments, thigh abduction-adduction joints 123 and 124 are located below hip flexion-extension joints 125 and 126. These joints are shown in greater detail in FIG. 10 which is a partial view of the same embodiment of FIG. 9.

Figure 10:
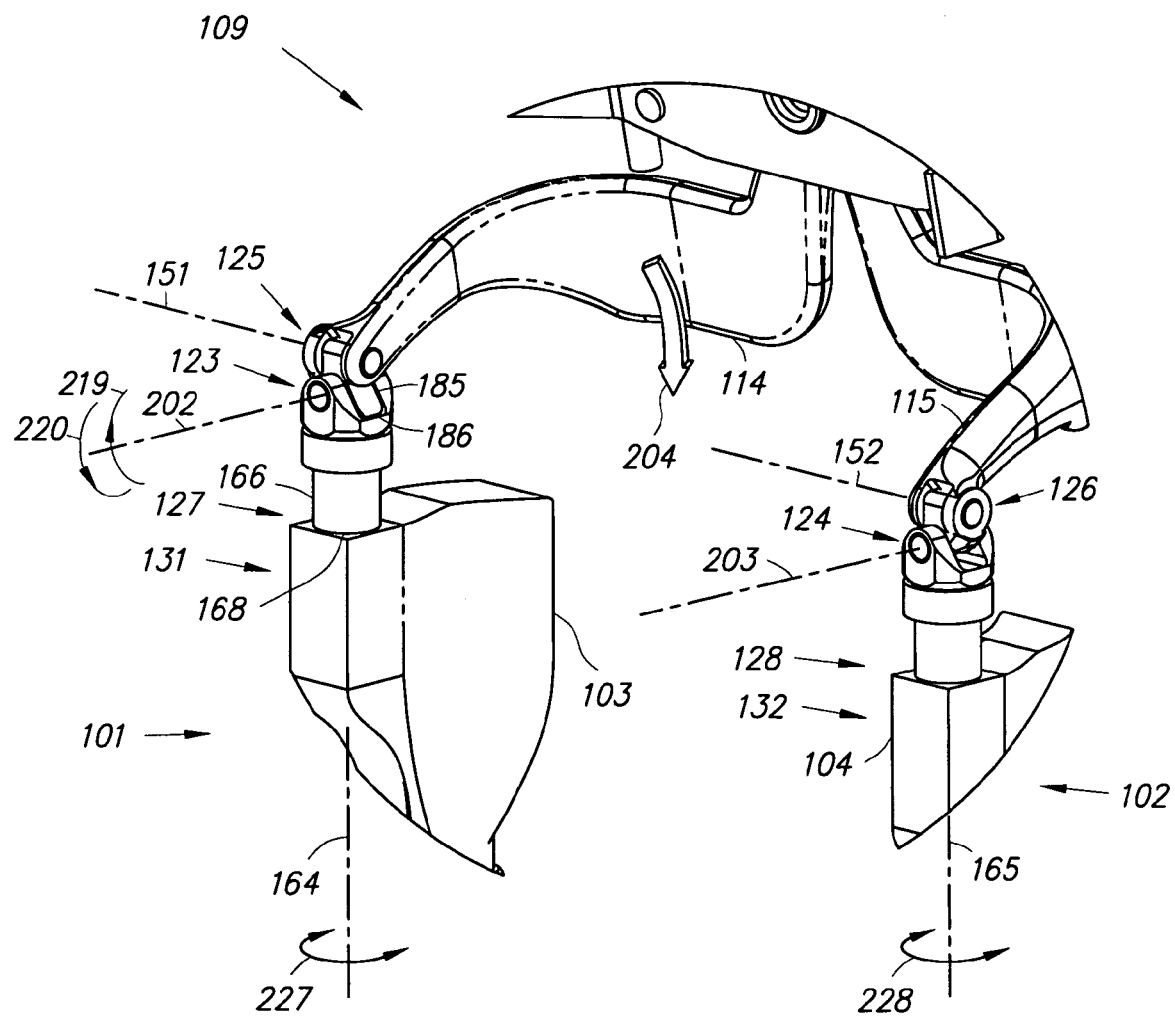
FIG. 10 is a partial view of the invention of the embodiment of FIG. 9.

In some embodiments of the invention, as shown in FIG. 10, leg supports 101 and 102 comprise a thigh adduction stop 185 which limits or prevents thigh links 103 and 104 from adducting at joint 123. Abduction and adduction of leg support 101 are shown by arrows 219 and 220 respectively. In the particular embodiment shown in FIG. 10, thigh abduction-adduction joint 123 includes a thigh adduction stop 185 which bears on a thigh stop surface 186. Thigh adduction stop 185 limits the adduction of thigh abduction-adduction joint 123. The unrestricted adduction of thigh abduction-adduction joint 123 would cause hip link 114 to move downwardly along arrow 204 during stance thereby dropping (lowering) the load. Such abduction-only joints for joints 123 and 124 are useful in allowing the person to squat naturally.

Figure 11:
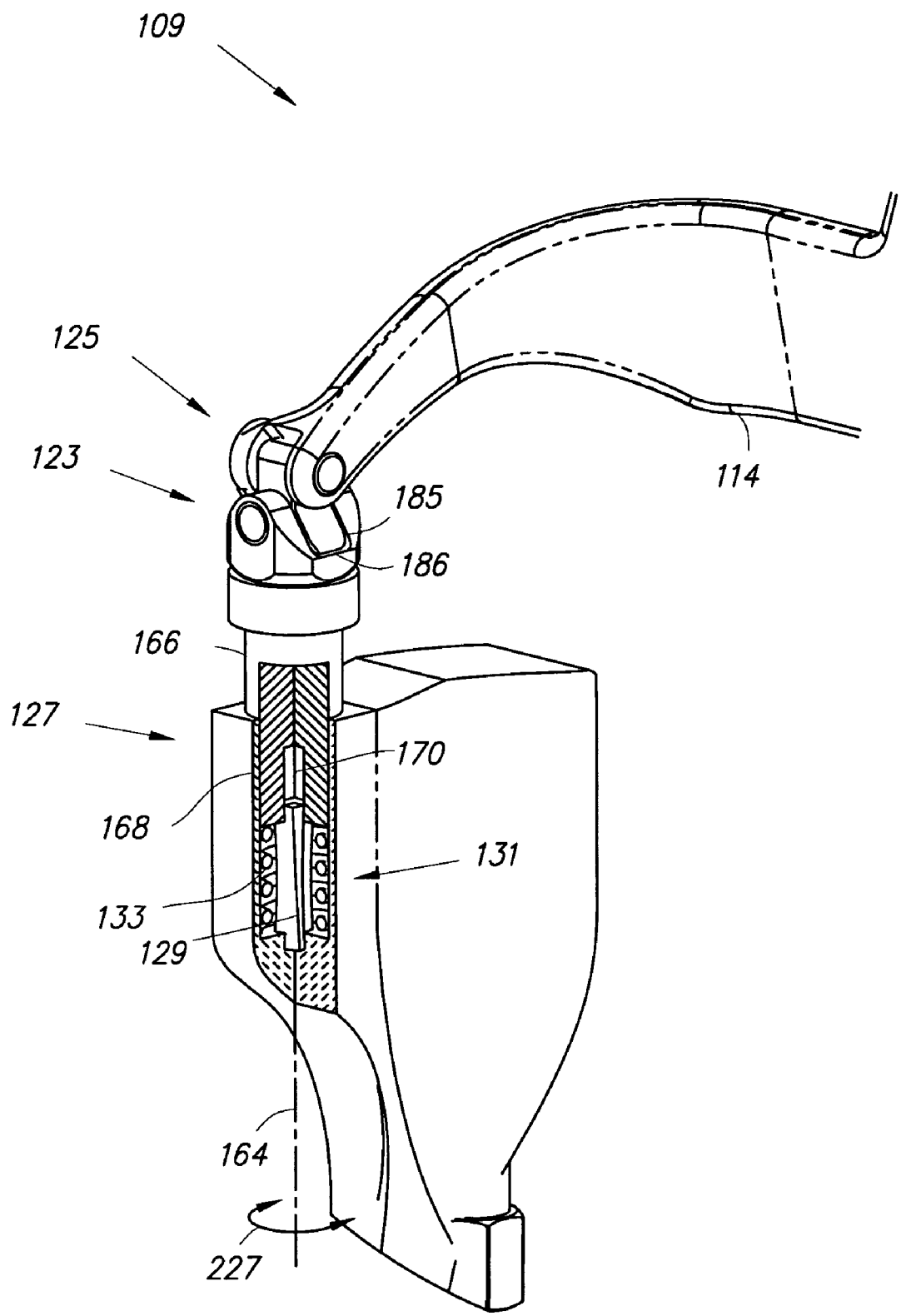
FIG. 11 is a partial view of the invention of the embodiment of FIG. 9.

In some embodiments, as shown in FIGS. 9 and 10, leg supports 101 and 102 further comprise leg rotation joints 127 and 128 configured to allow rotation of leg supports 101 and 102. In some embodiments, leg rotation joints 127 and 128 are located above knee joints 107 and 108. Lines 164 and 165 in FIG. 10 represent the rotation axes of leg rotation joints 127 and 128. In FIGS. 10 and 11, this is accomplished by providing for a sliding contact between the hip rotation shaft 166 and the hip rotation journal 168. Arrows 227 and 228 represent the leg rotational motion around axes 164 and 165. The parts included in the joint which prevent it from pulling apart have been omitted for simplicity, but one skilled in the art will note that there are many ways of retaining such shafts in such journals.

In some embodiments, as shown in FIG. 11, leg rotation joint 127 includes a leg rotation resilient element 129. This leg rotation resilient element provides a restoring torque which generally restores the leg back to a neutral position. Leg rotation resilient element 129 can be constructed in many ways, with the particular cross section shown in FIG. 11 being advantageous when using an elastomeric material to construct the element. Leg rotation resilient element 129 is shown partially deflected for illustration purposes.

Also, in some embodiments, as shown in FIG. 10 and FIG. 11, leg supports 101 and 102 further comprise compression-elongation mechanisms 131 and 132 configured to change the distance between exoskeleton trunk 109 and the respective knee flexion-extension joints 107 and 108. In some embodiments, compression-elongation mechanisms 131 and 132 allow for changes in the distance between the hip flexion-extension joints 125 and 126 and the respective knee flexion-extension joints 107 and 108. The compression-elongation mechanisms contracts by hip rotation shaft 166 sliding further into the hip rotation journal 168 (shown for leg 101 only). The leg rotation resilient element 129 is allowed to slide into a clearance cavity 170. In some embodiments, compression-elongation mechanism 131 and 132 further comprise a leg compression-elongation resilient element 133. This leg compression-elongation resilient element acts as a spring and provides a restoring force which generally restores the leg support back to a neutral configuration. In the embodiment of FIG. 11, this is illustrated by a helical spring.

Figure 12:
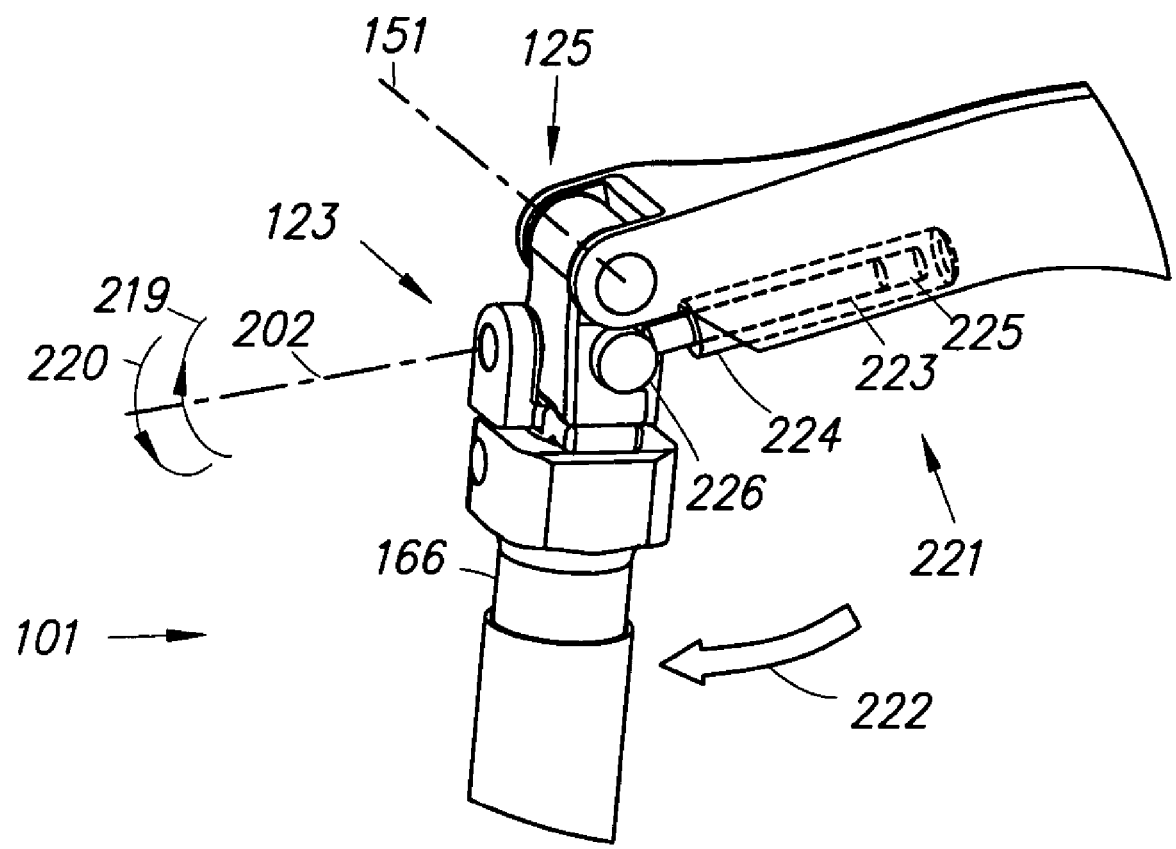
FIG. 12 is a perspective drawing in accordance with an embodiment of the present invention.

In some embodiments, as shown in FIG. 12, lower extremity exoskeleton 100 further comprises two swing resilient elements configured to apply torque between thigh links 103 and 104 and exoskeleton trunk 109. In operation swing resilient element 221 pushes leg link 101 forward along arrows 222 during swing phase. This allows the person to swing the thigh links forward with less effort. Gas spring 221 includes a gas spring piston 223 and a gas spring cylinder 224. In operation the force of compressed gas 225 in gas spring cylinder 224 forces gas spring piston 223 against cam 226 thereby pushing leg link 101 along arrow 222. Examples of a swing resilient element, 221, include, without limitation, extension spring, compression spring, leaf spring, gas spring, air spring, rubber, elastomer, surgical tube, bungee cord and combinations thereof. The stiffness of swing resilient element 221 may be chosen to give appropriate level of comfort.

In some embodiments, as shown in FIG. 9, exoskeleton trunk cover 171 may cover some components of exoskeleton trunk 109 including parts of hip links 114 and 115. The operation of the exoskeleton trunk is the same as in FIGS. 3 or 6 depending on the preferred choice of hip resilient element 116 or hip abduction-adduction resilient elements 121 and 122.

In some embodiments as shown in FIG. 9, thigh links 103 and 104 comprise thigh holding devices 135 and 136 configured to allow person 187 to couple to leg supports 101 and 102. Each thigh holding device 135 or 136 comprises an element or combination of elements including, without limitation, straps, bars, c-shape brackets, body cast, and elastomers. In some embodiments, as shown in FIG. 1, shank links 105 and 106 include comprise holding devices 137 and 138 configured to allow person 187 to couple to leg supports 101 and 102. Each shank holding device 137 and 138 comprises an element or combination of elements including, without limitation, straps, bars, c-shape brackets, body cast, and elastomers.

In some embodiments exoskeleton 100 comprises two torque generators 110 and 111 which are configured to allow flexion of knee joints 107 and 108 during swing phase, and resist flexion of knee joints 107 and 108 during stance phase, thereby allowing the lower extremity exoskeleton 100 to bear a load and transfer the load forces (e.g., load weight) to the ground.

In some embodiments, torque generators 110 and 111 are hydraulic torque generators. In accordance with embodiments shown in FIG. 1, through FIG. 9 torque generators 110 and 111 are hydraulic piston cylinders where the motion of the piston relative to the cylinder creates hydraulic fluid flow into or out of the cylinder. In operation, the hydraulic fluid flow into or out of the cylinder may be controlled by a hydraulic valve. The smaller the hydraulic valve orifice size is set, the more force is needed to move the piston relative to the cylinder with a given speed. In other words, the more damped the motion of the piston relative to the cylinder needs to be, the smaller the hydraulic valve orifice size should be. If the hydraulic valve orifice size is set to be large, then a small force is required to move the piston relative to the cylinder. Here impedance of hydraulic torque generator 110 or 111 is defined as the ratio of the required force over the velocity in frequency domain. With this definition, the smaller the hydraulic valve orifice size is chosen to be, the larger the impedance of the hydraulic torque generator will be.

In some embodiments, as shown in FIG. 13, torque generators 110 and 111 are hydraulic rotary dampers where produced torque may be controlled by a hydraulic valve. The smaller the hydraulic valve orifice size is set, the more torque is needed to rotate the hydraulic rotary damper with a given speed. In other words, the more damped the rotation of the hydraulic rotary damper needs to be, the smaller the hydraulic valve orifice size should be. Here impedance of hydraulic rotary dampers 110 or 111 is defined as the ratio of the required torque over the angular velocity in frequency domain. With this definition, the smaller the hydraulic valve orifice size is chosen to be, the larger the impedance of the hydraulic rotary damper will be.

In some embodiments torque generators 110 and 111 are friction brakes where one can control the resistive torque on knee joints 107 and 108 by controlling the friction torques. In other embodiments torque generators 110 and 111 are viscosity based friction brakes where one can control the resistive torque on knee joints 107 and 108 by controlling the viscosity of the fluid. In other embodiments, torque generators 110 and 111 are Magnetorheological Fluid Devices where one can control the resistive torque on knee joints 107 and 108 by controlling the viscosity of the Magnetorheological Fluid. One skilled in the art realizes that any of the above devices can be mounted in the invention to function in the same way as the hydraulic rotary dampers shown in FIG. 13.

Figure 14:
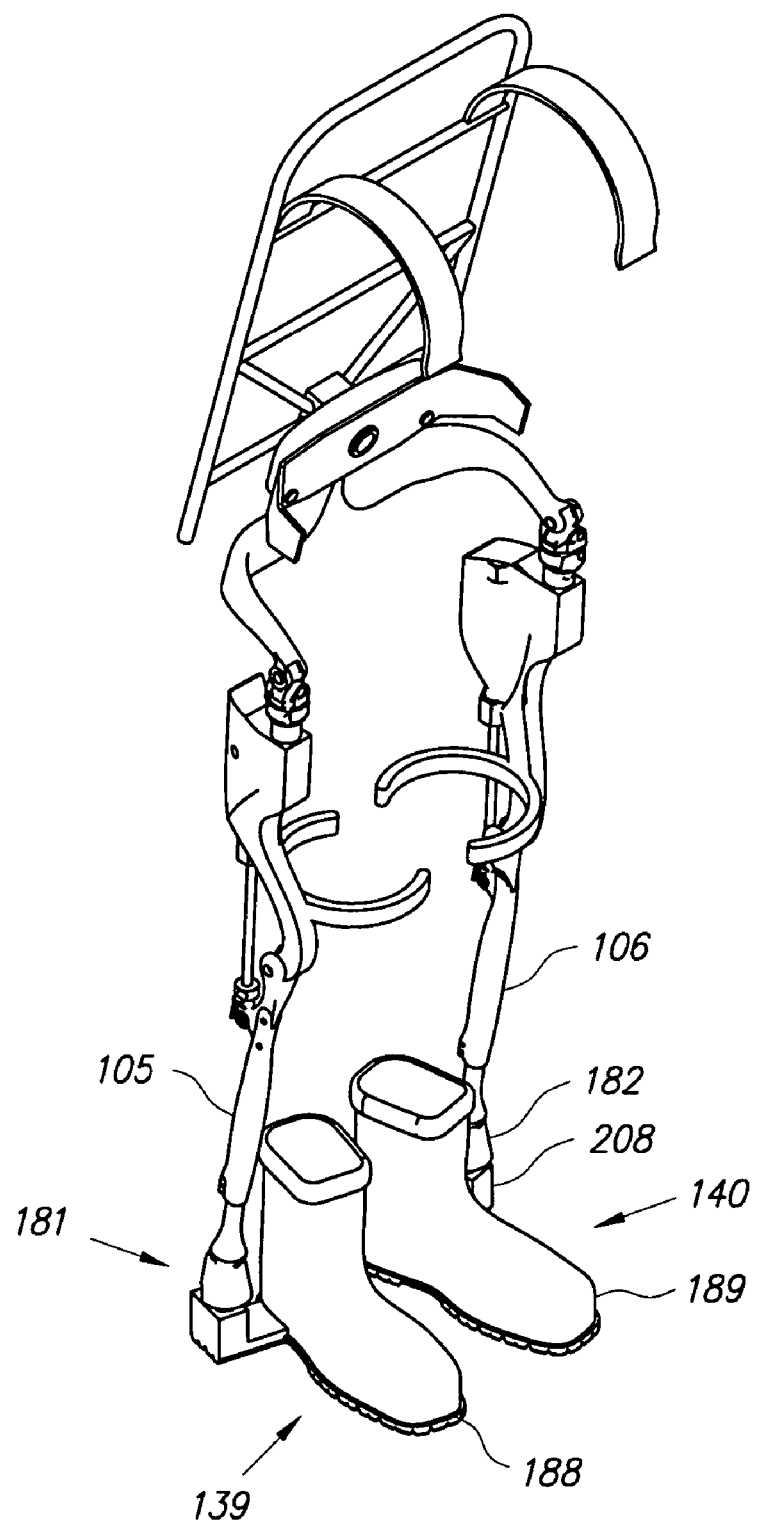
FIG. 14 is a perspective drawing in accordance with an embodiment of the present invention.
Figure 15:
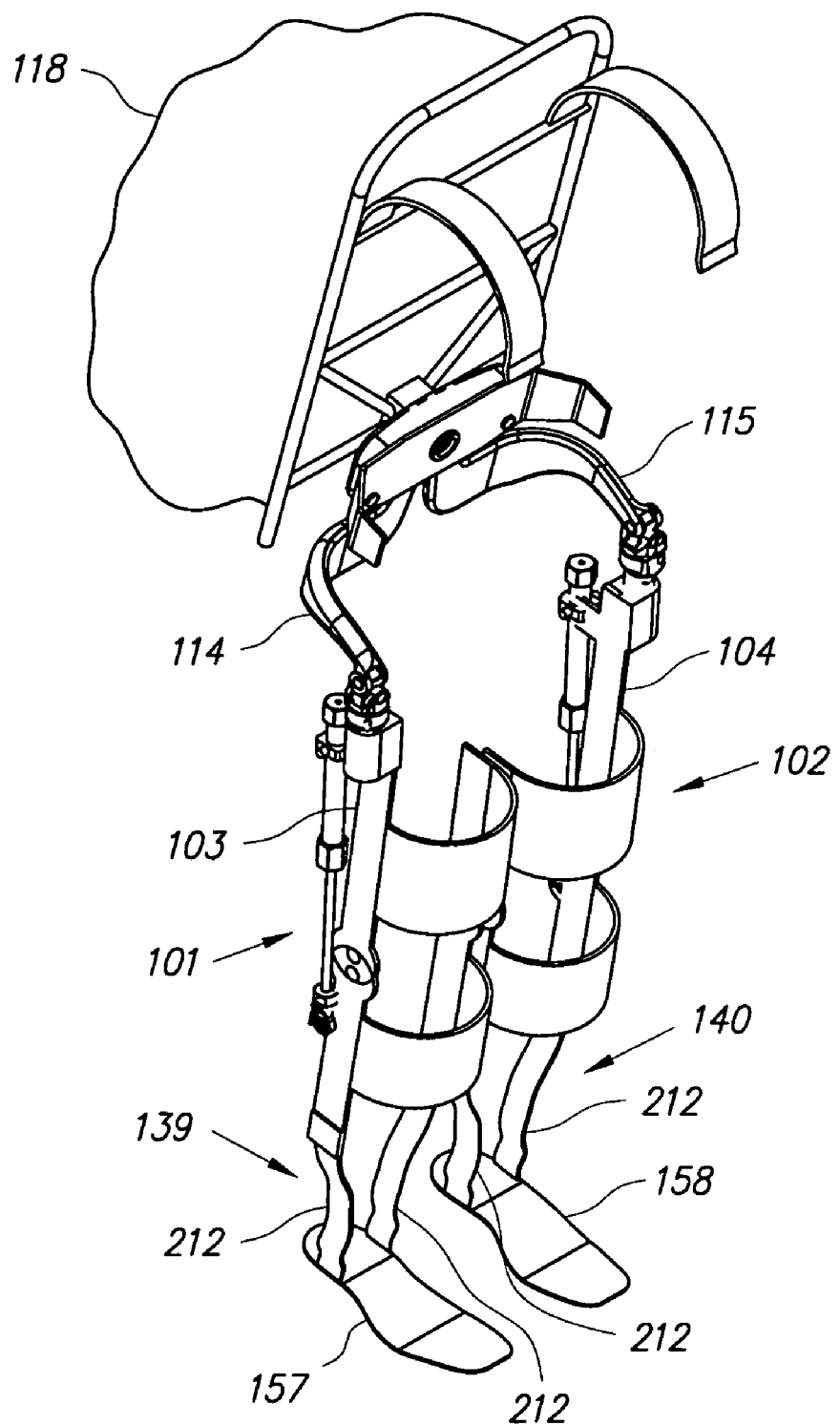
FIG. 15 is a perspective drawing in accordance with an embodiment of the present invention.

In some embodiments, as shown in FIG. 9, leg supports 101 and 102 further comprise exoskeleton feet 139 and 140 coupled to shank links 105 and 106 respectively, allowing the transfer of forces from shank links 105 and 106 to the ground. In operation, exoskeleton feet 139 and 140 are configurable to be coupled to the feet of person 187. In some embodiments, as shown in FIG. 9, the coupling to person's feet is accomplished by using clam-shell type bindings 205 and 206 sometimes found on modern snow shoes. However, there are a great number of methods to make such a connection as can be seen on different types of snow skis, snowboards, snowshoes and other such devices. In some embodiments, as shown in FIG. 14, exoskeleton feet 139 and 140 comprise exoskeleton shoes 188 and 189 wearable by person 187 thereby allowing exoskeleton feet 139 and 140 to couple to the feet of person 187. In some embodiments, as shown in FIG. 15, exoskeleton feet 139 and 140 comprise exoskeleton insoles 157 and 158 insertable inside the person's shoes, allowing exoskeleton feet 139 and 140 to couple to the feet of person 187. Insoles 157 and 158 are flexible and therefore can bend to match the curvature of the human foot during maneuvers such as squatting. Also, the insole side supports 212 are either compliant or configured to include degrees of freedom to mimic the movement of the human ankle.

Figure 16:
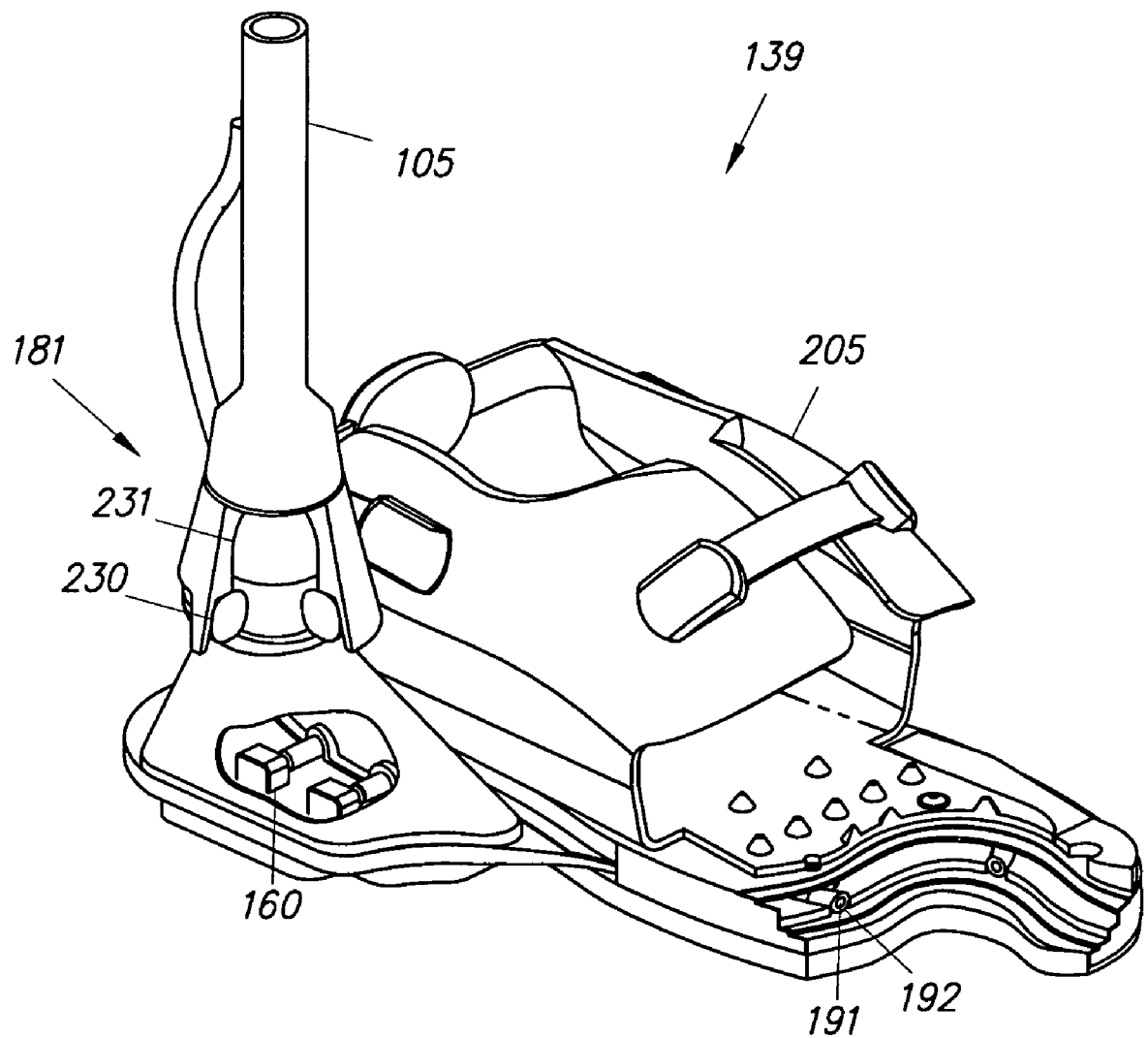
FIG. 16 is a perspective drawing in accordance with an embodiment of the exoskeleton foot.

In some embodiments, as shown in FIG. 9, exoskeleton feet 139 and 140 are compliantly coupled to shank links 105 and 106. This is accomplished using ankle compliant elements 181 and 182. FIG. 16 shows a close-up view of exoskeleton feet 139. In this example, ankle compliant elements 181 (and 182) each are constructed of a metal ball-and-socket joint 231 surrounded by an elastomer donut shape element 230 which creates compliance in all directions of rotations.

Figure 17:
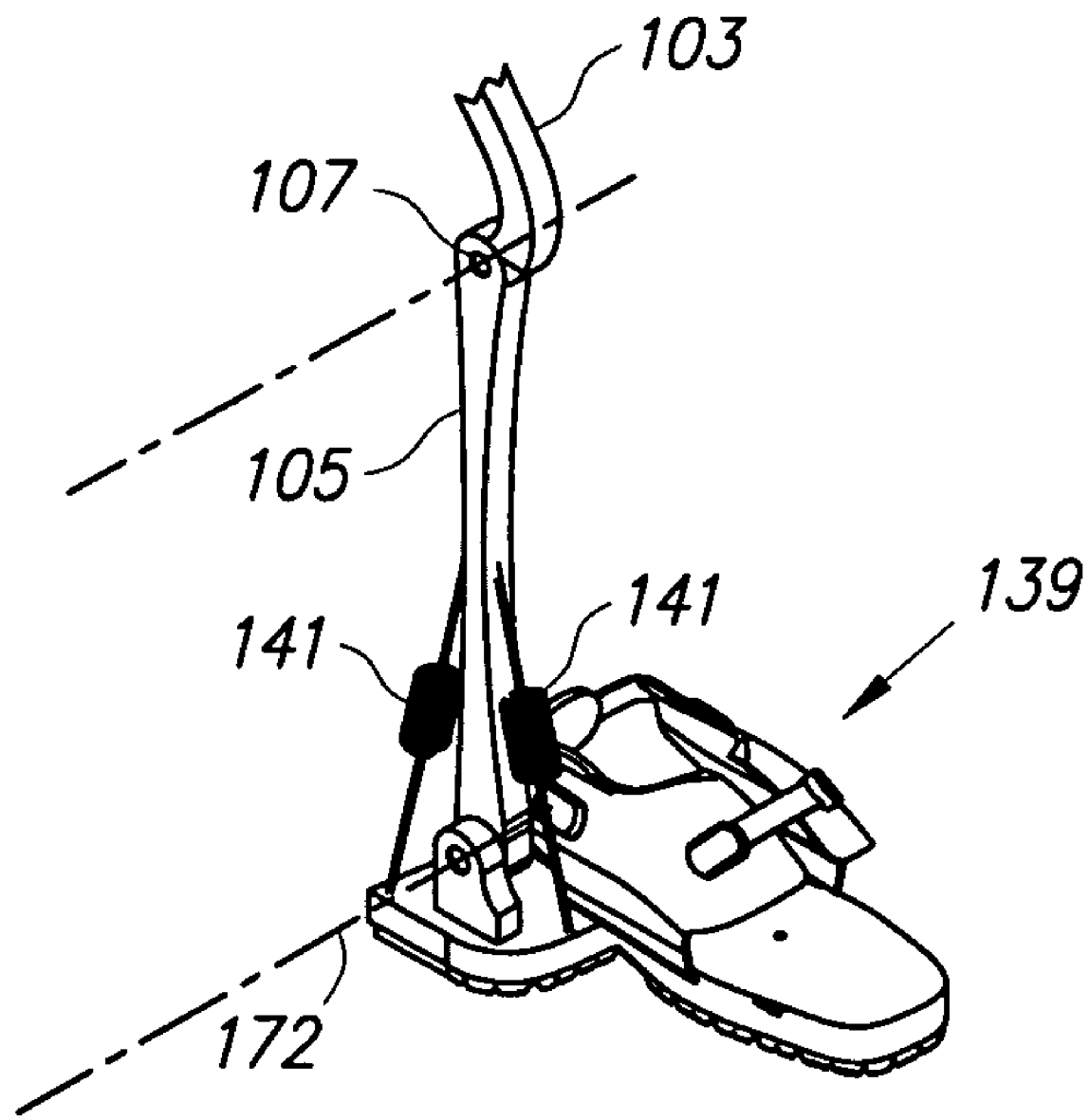
FIG. 17 is a perspective drawing in accordance with an embodiment of the exoskeleton foot.

In some embodiments, exoskeleton feet 139 and 140 rotate about two plantar-dorsi flexion axes relative to shank links 105 and 106. FIG. 17 shows an embodiment of this type of exoskeleton where ankle plantar-dorsi flexion axis 172 is generally parallel to the plantar-dorsi flexion axis in the human ankle. In some embodiments, each leg support further comprises at least one ankle plantar-dorsi flexion resilient element 141 resisting the rotation of respective exoskeleton foot about ankle plantar-dorsi flexion axis 172.

Figure 18:
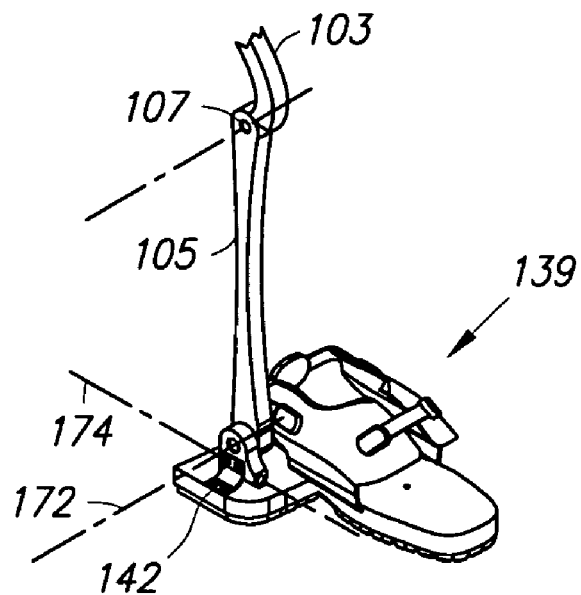
FIG. 18 is a perspective drawing in accordance with an embodiment of the exoskeleton foot.

In some embodiments, as shown in FIG. 18, exoskeleton feet 139 and 140 rotate about two abduction-adduction axes 174 and 175 relative to shank links 105. FIG. 18 shows an embodiment of this type of exoskeleton where ankle abduction-adduction axis 174 is generally parallel to the abduction-adduction axis in the human ankle. In some embodiments each leg support further comprises at least one ankle abduction-adduction resilient element 142 resisting the rotation of exoskeleton foot 139 about ankle abduction-adduction axis 174.

Figure 19:
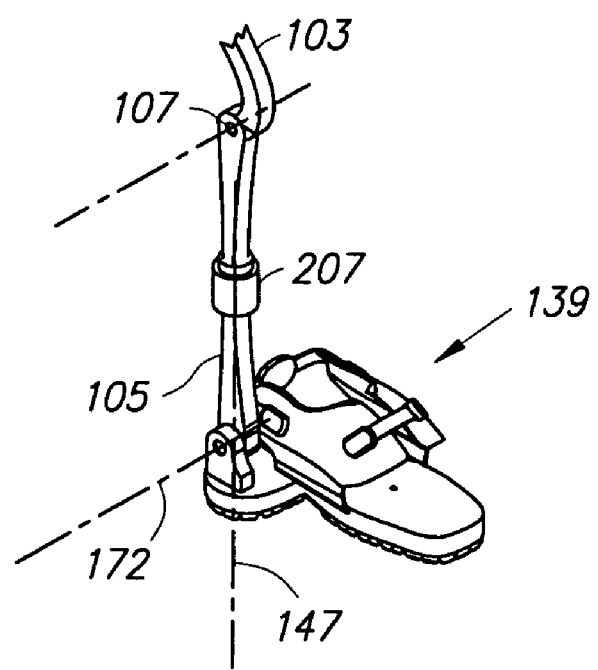
FIG. 19 is a perspective drawing in accordance with an embodiment of the exoskeleton foot.

In some embodiments, as shown in FIG. 19, exoskeleton feet 139 and 140 rotate about two rotation axes 147 and 148 relative to shank links 105 and 106. In some cases, this is accomplished using a shank rotation joint 207 which functions similar to leg rotation joint 127. FIG. 19 shows an embodiment of this type of exoskeleton where ankle rotation axis 147 is generally parallel to the rotation axis in the human ankle. In some embodiments, resilient elements can be included in the ankle to resist the rotation of the exoskeleton foot 139 about ankle rotation axis 147.

Figure 20:
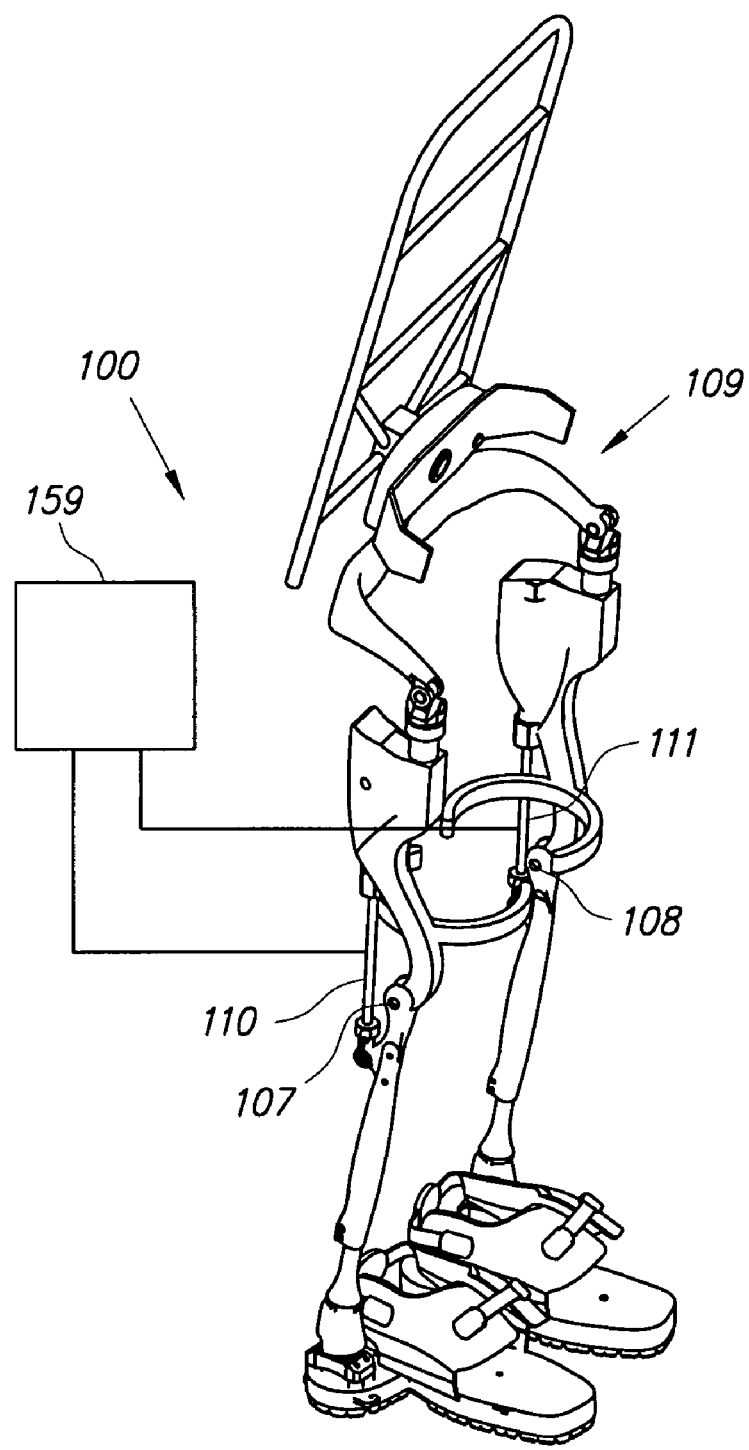
FIG. 20 is a perspective drawing in accordance with an embodiment of the invention.

In some embodiments, as shown in FIG. 20, lower extremity exoskeleton 100 further comprises controller 159 configured to control torque generators 110 and 111. Controller 159, in some embodiments, is mounted to exoskeleton trunk 109. In some embodiments controller 159 is mounted to torque generators 110 and 111. Controller 159 may be a simple mechanical device consisting of hydraulic or pneumatic circuitry or it may include electronic elements as well.

Figure 21:
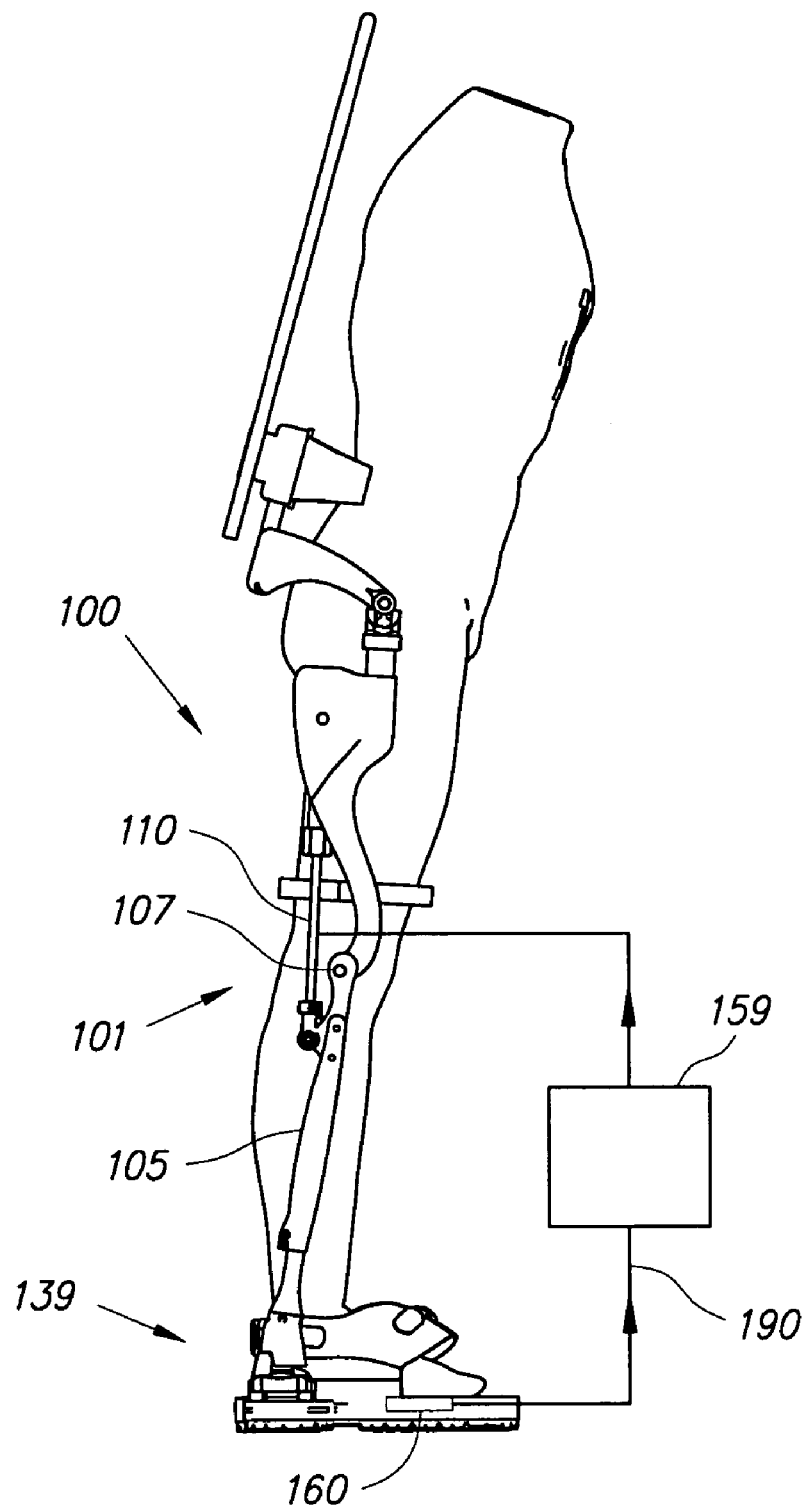
FIG. 21 is a perspective drawing in accordance with an embodiment of the invention.

In some embodiments, as shown in FIG. 21, exoskeleton 100 comprises at least one foot sensor 160 per leg support which produces a stance signal 190 representing the force on the bottom of each foot of person 187. The information from foot sensor 160 identifies whether the foot of person 187 is in a stance phase or in a swing phase. Controller 159 controls the torque generators 110 and 111 as a function of the signals from the respective foot sensors.

Figure 22:
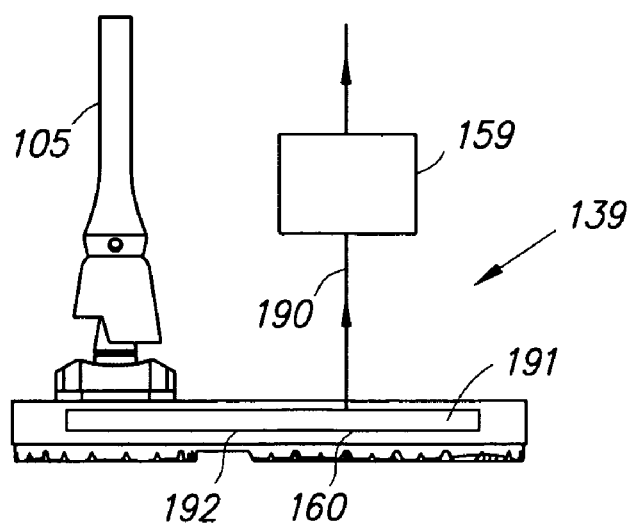
FIG. 22 is a drawing in accordance with an embodiment of the exoskeleton foot.

In some embodiments, as shown in FIG. 22, foot sensors 160 are integrated into exoskeleton feet 139 and 140. In some embodiments, as shown in FIG. 22, foot sensor 160 is a pressure sensor measuring the pressure in a media 191 trapped in a foot sensor cavity 192 inside exoskeleton foot 139. FIG. 16 shows an embodiment where a tube is used as a foot sensor cavity 192. Pressure sensor 160 measures the pressure in a media 191 trapped in a foot sensor cavity 192. In some cases, the stance signal 190 may take the form of the media 191 itself ported in a small tube from the cavity 192 to the controller 159 where the pressure in the media is used to move a mechanical valving in response to person's force on exoskeleton feet 139 and 140. In that case, no electronics would be required to construct controller 159.

Figure 23:
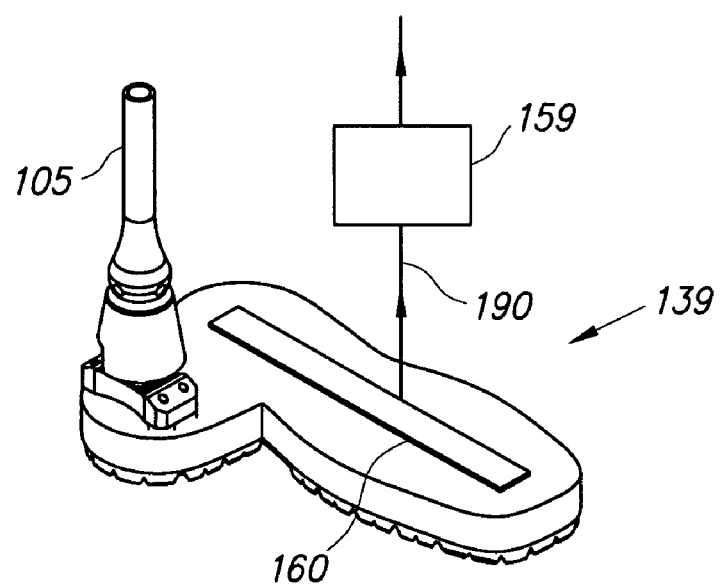
FIG. 23 is a drawing in accordance with an embodiment of the exoskeleton foot.
Figure 24:
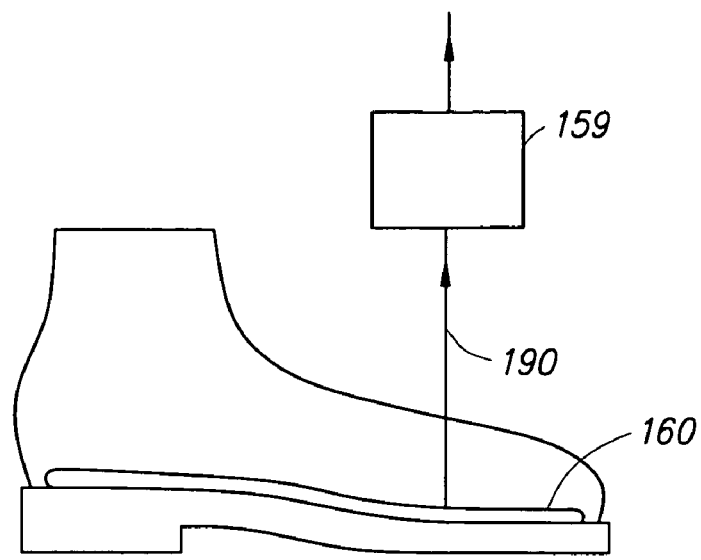
FIG. 24 is a drawing in accordance with an embodiment of the exoskeleton foot.
Figure 25:
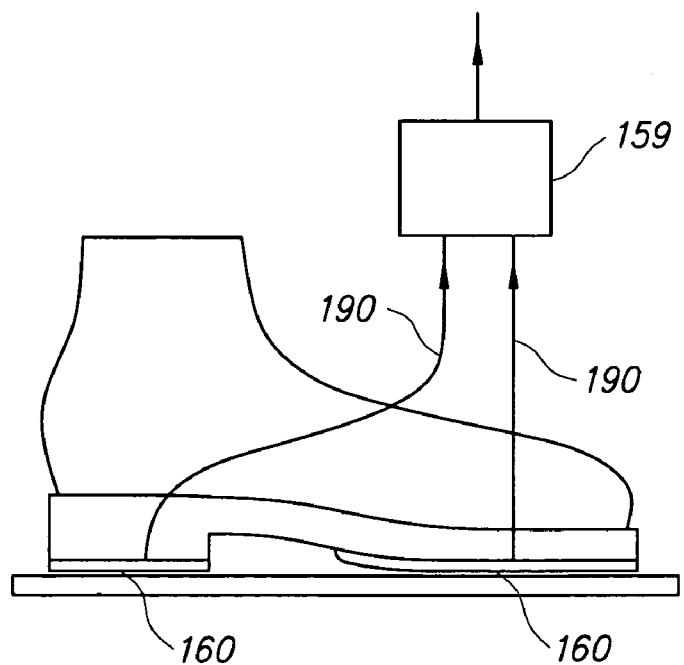
FIG. 25 is a drawing in accordance with an embodiment of the exoskeleton foot.
Figure 26:
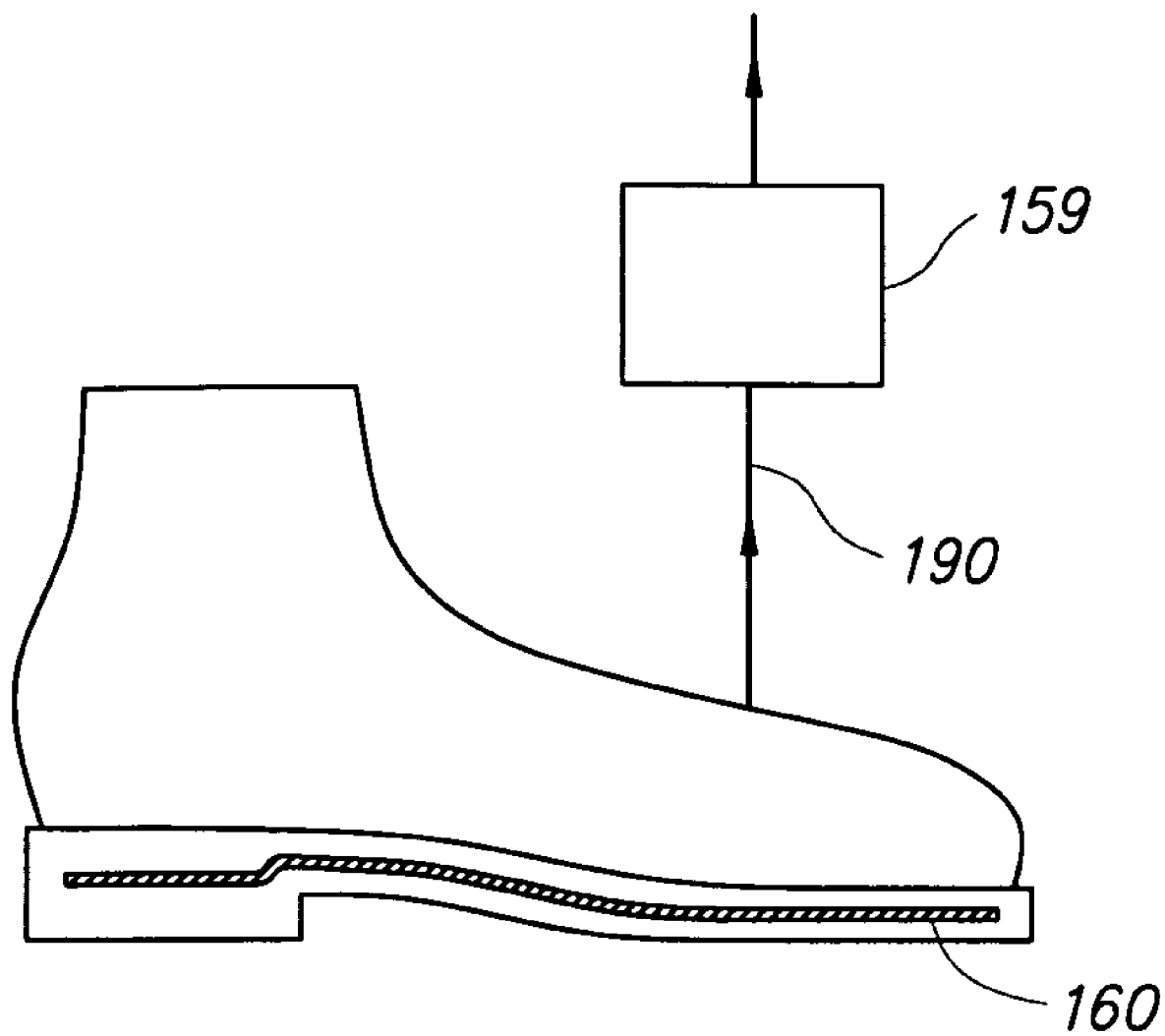
FIG. 26 is a drawing in accordance with an embodiment of the exoskeleton foot.

FIG. 23 shows another embodiment wherein foot sensor 160 is a force sensor connectable to exoskeleton foot 139. In some embodiments, as shown in FIG. 24, foot sensor 160 is located inside the human shoe like an insole and its output signal represents the force on the bottom of the human foot. This type would be particularly useful in embodiments of the invention such as those shown in FIG. 14 or 15. In some embodiments, as shown in FIG. 25, foot sensor 160 is connected to the bottom of the human shoe and senses the force on the bottom of the human foot. In some embodiments, as shown in FIG. 26, foot sensor 160 is located inside the human shoe sole and senses the force on the bottom of the human foot.

Foot sensor 160 comprises any sensor or combination of sensors capable of performing the indicated functions. Examples of foot sensor 160 include, without limitation, force sensors, strain-gage based force sensors, piezoelectric force sensors, force sensing resistors, pressure sensors, switches, tape switches and combinations thereof. In some embodiments foot sensor 160 is a switch that represents the existence of a force greater than some threshold force on the bottom of the foot of person 187.

Controller 159 controls the resistance to flexion in knee joints 107 and 108 as a function of the signals from the respective foot sensors. For example, when foot sensor 160 detects the stance phase in the right leg support, controller 159 will increase the impedance of torque generator 110 so knee joint 107 resists flexion. Conversely, when foot sensor 160 detects the swing phase, controller 159 will decrease the impedance of torque generator 110 so no resistance to flexion occurs in knee joint 107. Large impedances of torque generators 110 and 111 lead to large resistance of knee joints 107 and 108 to flexion needed during stance phase. Conversely, small impedances of torque generators 110 and 111 lead to small resistance of knee joints 107 and 108 to flexion needed during swing phase.

It is important to note that a foot sensor is not a requirement of the invention since there are other methods to determine when stance phase and swing phase are occurring. One such method is to sense when the knee hyperextends (as typically occurs when the leg support swings directly under the person's body during stance) and to assume that swing phase begins at that moment. The end of swing phase would then be estimated by detecting when the knee stops extending. To implement this strategy, controller 159 might be a simple mechanical/hydraulic device built into a hydraulic cylinder which uses the motion of the cylinder to actuate the valving within it.

Figure 27:
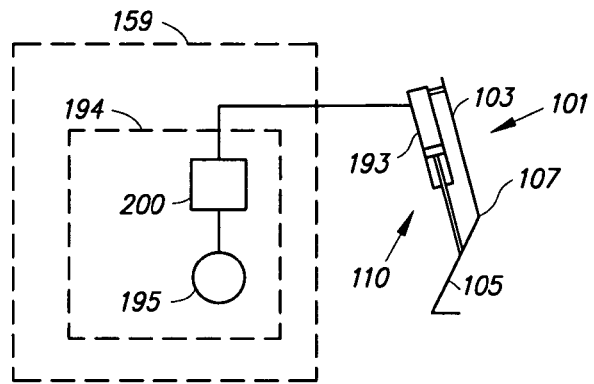
FIG. 27 is a drawing representing an embodiment of the exoskeleton hydraulic circuitry.

FIG. 27 shows an embodiment of the invention for leg support 101 where torque generator 110 comprises hydraulic piston-cylinder 193 and controller 159 includes a hydraulic circuitry 194 to control the fluid flow to hydraulic piston-cylinder 193. In general, during stance phase, hydraulic circuitry 194 restricts the fluid flow from hydraulic piston-cylinder 193. The restriction in the fluid flow leads to large impedance for the hydraulic piston-cylinder 193 and allows leg support 101 to resist flexion. Conversely, a small restriction in the fluid flow leads to small impedance for piston-cylinder 193 and allows leg support 101 to flex easily.

In some embodiments, controller 159 controls the fluid flow from hydraulic piston-cylinder 193 as a function of stance signal 190. Foot sensor 160 detects the force on the bottom of the person's foot when the person's foot is on the ground (stance phase). Controller 159 restricts the fluid flow from hydraulic piston-cylinder 193 based on received stance signal 190. The restriction in the fluid flow leads to a large impedance for the piston-cylinder 193 and allows leg support 101 to resist flexion. When foot sensor 160 detects that the person's foot is not on the ground (i.e., there is no force on the bottom of the person's foot), controller 159 decreases the restriction on the fluid flow to hydraulic piston-cylinder 193. A small restriction on the fluid flow leads to a small impedance for piston-cylinder 193 and allows leg support 101 to flex easily.

Figure 28:
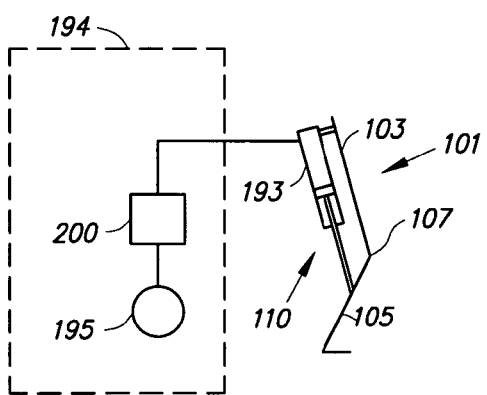
FIG. 28 is a drawing representing an embodiment of the exoskeleton hydraulic circuitry.

FIG. 28 shows an embodiment of the invention where hydraulic circuitry 194 comprises an actuated flow-restricting valve 200 connecting piston-cylinder 193 to a hydraulic reservoir 195. Controller 159 controls actuated flow-restricting valve 200. Actuated flow-restricting valve 200 increases the restriction on the fluid flow during stance phase and decreases the restriction on the fluid flow during swing phase.

Figure 29:
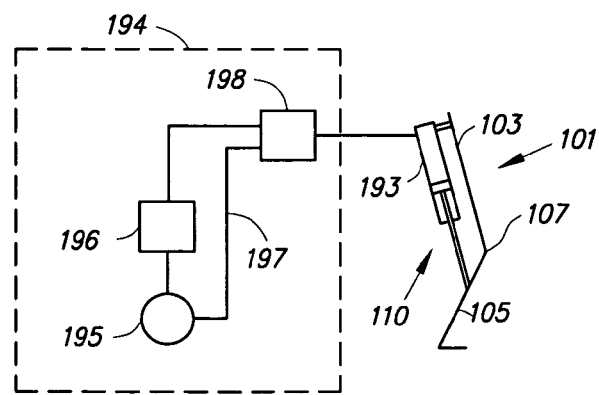
FIG. 29 is a drawing representing an embodiment of the exoskeleton hydraulic circuitry.

FIG. 29 shows an embodiment of the invention where hydraulic circuitry 194 comprises a hydraulic three-way valve 198 connecting piston-cylinder 193 to a hydraulic reservoir 195 either through a needle valve 196 or a bypass line 197. Hydraulic three-way valve 198 connects piston-cylinder 193 to hydraulic reservoir 195 through needle valve 196 during stance phase thereby restricting the hydraulic flow and increasing the impedance of piston-cylinder 193. During swing phase, hydraulic three-way valve 198 connects piston-cylinder 193 to hydraulic reservoir 195 through bypass line 197, thereby increasing the hydraulic fluid flow and decreasing the impedance of piston-cylinder 193.

Figure 30:
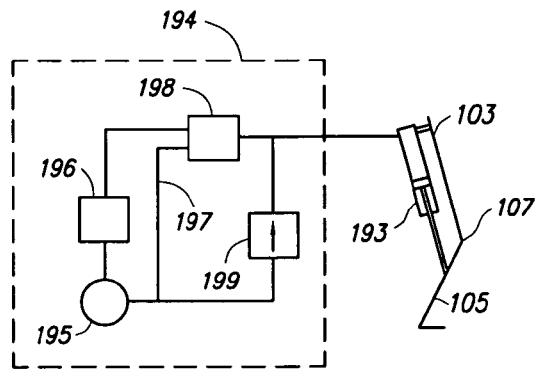
FIG. 30 is a drawing representing an embodiment of the exoskeleton hydraulic circuitry.

FIG. 30 represents another embodiment of the hydraulic circuitry 194. This embodiment is similar to the embodiment of FIG. 29 but an additional check valve 199 has been added to allow the knee to extend easily (no or minimum resistance) at all times.

Figure 31:
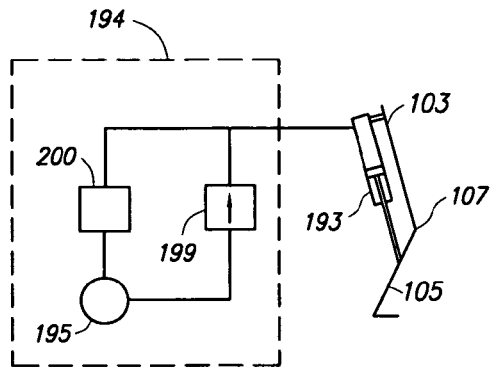
FIG. 31 is a drawing representing an embodiment of the exoskeleton hydraulic circuitry.

FIG. 31 represents another embodiment of the hydraulic circuitry 194 where an actuated flow-restricting valve 200 capable of controlling its orifice size and a check valve 199 connect piston-cylinder 193 to hydraulic reservoir 195. During stance phase controller 159 restricts the fluid flow by controlling the orifice of actuated flow-restricting valve 200. During swing phase controller 159 opens actuated flow-restricting valve 200 and allows for fluid flow to piston-cylinder 193 thereby decreasing the impedance of piston-cylinder 193. Actuated flow-restricting valve 200 comprises any valve or combination of valves capable of performing the indicated functions. Examples of actuated flow restricting valve 200 include, without limitation, flow control valves, pressure control valves and on-off valves. Check valve 199 allows knee joint 107 to extend easily at all times.

Figure 32:
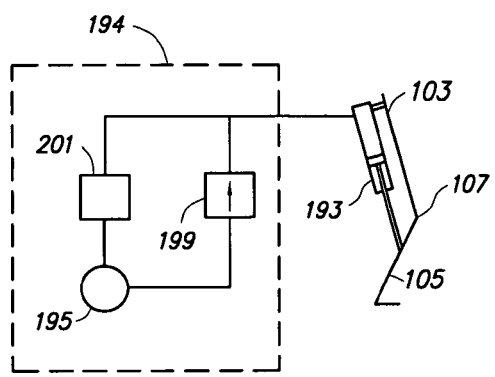
FIG. 32 is a drawing representing an embodiment of the exoskeleton hydraulic circuitry.

FIG. 32 represents another embodiment of the hydraulic circuitry 194 where a two-way valve 201 capable of selecting between a set orifice size or fully open orifice, and check valve 199 connect piston-cylinder 193 to hydraulic reservoir 195. During stance phase controller 159 directs the fluid flow to piston-cylinder 193 through the set orifice size of two-way valve 201. During swing phase controller 159 directs the fluid flow to piston-cylinder 193 through fully open orifice of two-way valve 201. Check valve 199 allows knee joint 107 to extend easily at all times.

Figure 33:
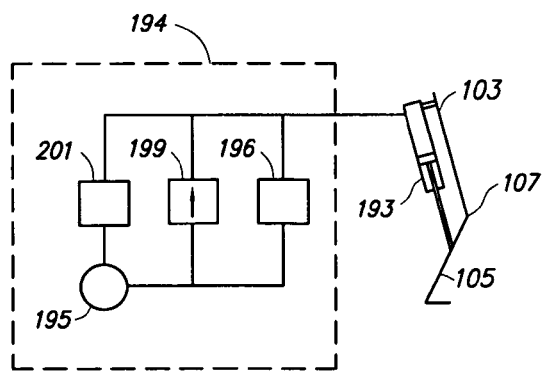
FIG. 33 is a drawing representing an embodiment of the exoskeleton hydraulic circuitry.

FIG. 33 represents another embodiment of the hydraulic circuitry 194 where a two-way valve 201, a check valve 199, and a needle valve 196 connect piston-cylinder 193 to hydraulic reservoir 195. During stance phase, controller 159 blocks the fluid flow in two-way valve 201 and therefore flow reaches piston-cylinder 193 through needle valve 196. During swing phase controller 159 opens two-way valve 201 and allows for minimum resistance. Check valve 199 allows knee joint 107 to extend easily at all times. Needle valve 196 may be manually or automatically adjusted.

Figure 34:
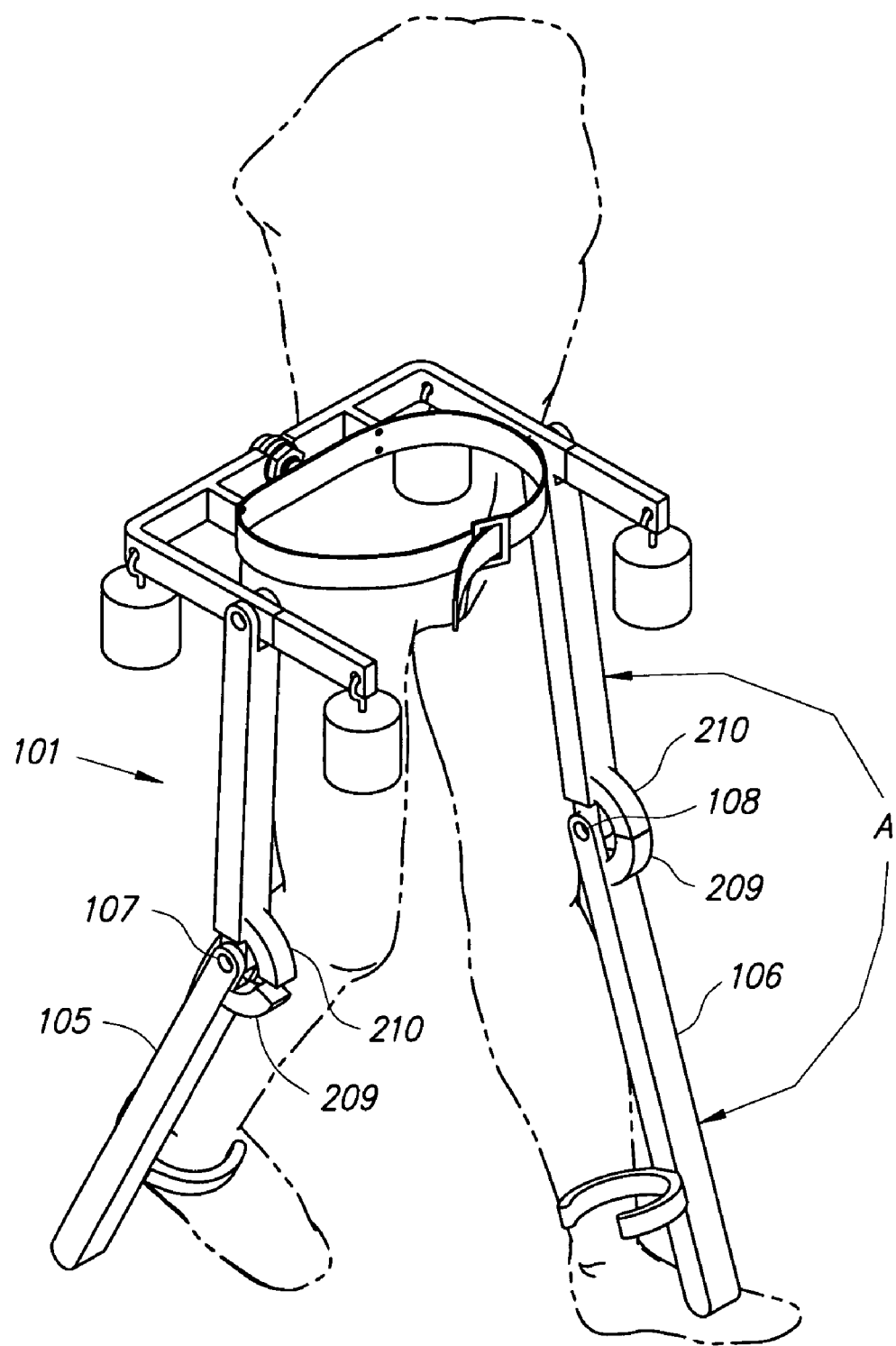
FIG. 34 is a perspective drawing in accordance with an embodiment of the invention.

In some embodiments leg support 101 and 102 is configured to allow flexion of the respective knee joint during the swing phase, and to resist flexion of the respective knee joint during the stance phase by locking the knees. One such locking knee is shown in FIG. 34. In the figure, the shank link 105 includes a shank stop 209 which bears on thigh stop 210 when the knee is hyperextended. The angle of the knee at hyperextension is illustrated as A in the FIG. 34. Since this angle is less than 180 degrees, the knee joint 107 or 108 will go "over-center" when approaching hyper-extension, meaning that the knee will tend to lock against the stops if the leg supports 101 and 102 is subject to a compressive load, as would be the case for leg support 102 in the situation illustrated in the figure. One skilled in the art will note that there are many such over-center mechanisms which generally tend to force the load vector on the leg support to pass in front of the knee joint.

Figure 35:
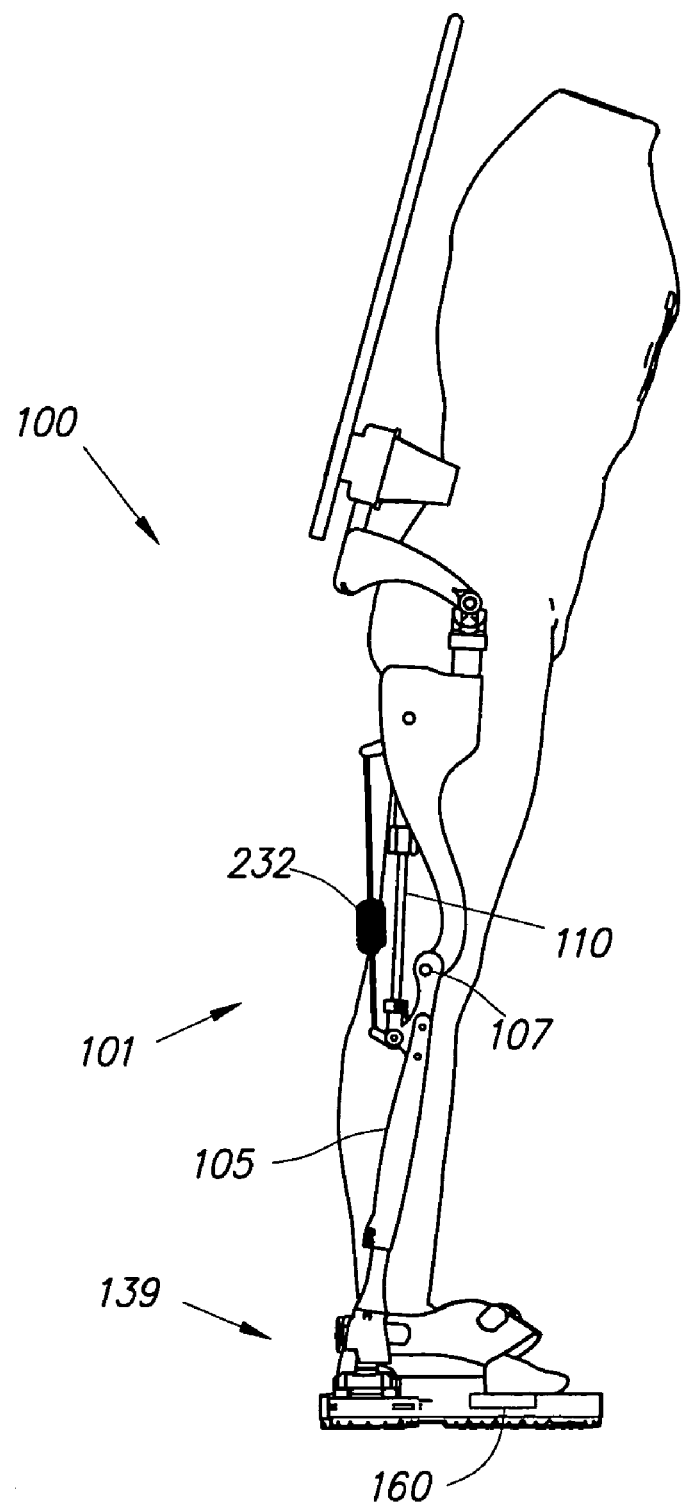
FIG. 35 is a drawing representing an embodiment of the exoskeleton.
Figure 36:
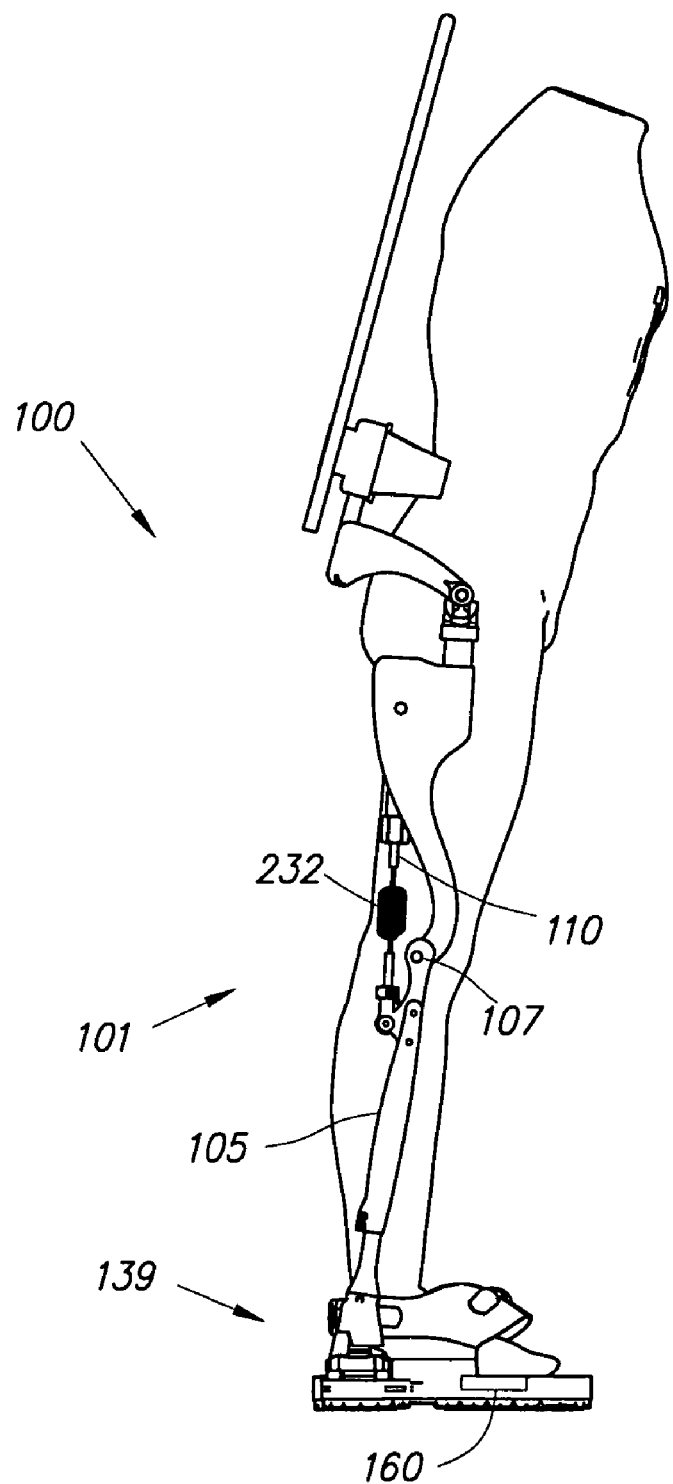
FIG. 36 is a drawing representing an embodiment of the exoskeleton.

In some embodiments, exoskeleton 100 further comprises knee resilient elements 232 which are configured to encourage flexion of knee joints 107 and 108. This decreases the person's effort needed to flex knee joints 107 and 108 during the swing phase. In some embodiments, as shown in FIG. 35, resilient elements 232 are in parallel with torque generators 110 and 111 if any torque generators are included in the exoskeleton. In some embodiments resilient elements 232, as shown in FIG. 36, are in series with torque generators 110 and 111 if any torque generators are included in the exoskeleton. In some embodiment, exoskeleton 100 comprises knee resilient elements 232 which are configured to encourage extension of knee joints 107 and 108. One skilled in the art will note that there are many methods and locations for installation of resilient element 232 to encourage flexion and/or extension of knee joint 107. It is further understood that knee resilient elements 232 can also be used with the embodiment of the exoskeleton shown in FIG. 34.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A lower extremity exoskeleton, configurable to be coupled to a person, said lower extremity exoskeleton comprising:
    two leg supports configurable to be coupled to said person's lower limbs and configured to rest on the ground during their stance phases where each said leg support comprises a leg rotation joint configured to allow rotation of said leg support, a thigh link and a shank link;
    two knee joints, each configured to allow flexion and extension between respective shank link and respective thigh link; and
    an exoskeleton trunk, configurable to be coupled to said person's upper body, rotatably connectable to said thigh links of said leg supports allowing for the flexion and extension between said leg supports and said exoskeleton trunk;
    wherein the entire energy required for said flexion and extension between the shank link and the respective thigh link of a leg support over a cyclic knee motion is provided by said person.

2. The device of claim 1 wherein each said leg support is configured to allow flexion of said respective knee joint during a swing phase, and to resist flexion of said respective knee joint during the stance phase to allow the transfer of a force to the ground.

3. The device of claim 1 wherein the energy required for flexion and extension movement between a thigh link and said exoskeleton trunk over a cyclic hip motion is provided by said person.

4. The device of claim 1 wherein said exoskeleton trunk further allows for rotation of each said leg support about an abduction-adduction axis generally parallel to ground.

5. The device of claim 1 wherein said exoskeleton trunk further comprises two hip links rotatably connectable to said respective thigh links to allow for said flexion and extension of said support legs relative to said exoskeleton trunk; wherein said hip links are rotatably connected to each other to allow for abduction of the leg supports.

6. The device of claim 1 wherein said exoskeleton trunk further comprises two hip links rotatably connectable to said respective thigh links to allow for said flexion and extension of said support legs relative to said exoskeleton trunk; wherein said hip links are rotatably connected to each other to allow for adduction of the leg supports.

7. The device of claim 1 wherein said exoskeleton trunk is configured to hold a rear load behind said person when said exoskeleton trunk is coupled to said person's upper body.

8. The device of claim 1 wherein said exoskeleton trunk further comprises an extension frame configured to hold a front load in front of said person when said exoskeleton trunk is coupled to said person's upper body.

9. The device of claim 5 wherein said exoskeleton trunk further comprises a hip resilient element configured to apply a torque between said hip links.

10. The device of claim 6 wherein said exoskeleton trunk further comprises a hip resilient element configured to apply a torque between said hip links.

11. The devices of claim 9 wherein said hip resilient element comprises an elastic element or combination of elastic elements selected from a group consisting of extension spring, compression spring, leaf spring, air spring, gas spring, rubber, elastomer, surgical tube, and bungee cord.

12. The devices of claim 10 wherein said hip resilient element comprises an elastic element or combination of elastic elements selected from a group consisting of extension spring, compression spring, leaf spring, air spring, gas spring, rubber, elastomer, surgical tube, and bungee cord.

13. The device of claim 5 wherein said exoskeleton trunk further comprises a hip abduction stop to limit the abduction of said hip links with respect to each other.

14. The device of claim 1 wherein said thigh link of each said leg support further includes a thigh abduction-adduction joint configured to allow abduction of said respective leg support.

15. The device of claim 14 wherein each said leg support further includes a hip flexion-extension joint allowing for the flexion and extension between each of said leg supports and said exoskeleton trunk, wherein said thigh abduction-adduction joints are generally located below said hip flexion-extension joints.

16. The device of claim 1 wherein said thigh of each said leg support further includes a thigh abduction-adduction joint configured to allow adduction of said leg support.

17. The device of claim 16 wherein each said leg support further includes a hip flexion-extension joint allowing for the flexion and extension between each of said leg supports and said exoskeleton trunk, and said abduction-adduction joints generally located below said hip flexion-extension joints.

18. The device of claim 1 wherein said leg rotation joints are generally located above said knee joints.

19. The device of claim 1 wherein each said leg rotation joints further comprise a leg rotation resilient element that provides a restoring torque which generally restores said leg support back to a neutral position.

20. The device of claim 1 each said leg support further includes a hip flexion-extension joint allowing for the flexion and extension between each of said leg supports and said exoskeleton trunk, wherein said thigh link of each said leg support further includes a compression-elongation mechanism configured to allow a change in the distance between said hip flexion-extension joint and said knee joint.

21. The device of claim 20 wherein said compression-elongation mechanism comprises a leg compression-elongation resilient element that provides a restoring force which generally restores said leg support back to a neutral configuration.

22. The device of claim 1 further comprising two swing resilient elements configured to apply torque between said thigh links and said exoskeleton trunk.

23. The device of claim 1 wherein said thigh links include thigh holding devices configured to allow said person to couple to said leg supports.

24. The device claim 23 wherein each said thigh holding device comprises an element or combination of elements selected from a group consisting of strap, bar, c-shape brackets, body cast and elastomers.

25. The device of claim 1 wherein said shank links include shank holding devices configured to allow said person to couple to said leg supports.

26. The device claim 25 wherein each said shank holding device comprises an element or combination of elements selected from a group consisting of strap, bar, c-shape brackets, body cast and elastomers.

27. The device of claim 1 wherein each said leg support further comprises an exoskeleton foot configured to be coupled to respective said person's foot and coupled to respective said shank link to allow the transfer of forces from said shank link to the ground.

28. The device of claim 1 wherein each said leg support further comprises an exoskeleton foot coupled to respective said shank link and configured to be coupled to the bottom of the said respective person's shoe to allow the transfer of forces from said shank link to the ground.

29. The device of claim 27 wherein each said exoskeleton foot further comprises a shoe wearable by said person to allow said exoskeleton foot to couple said person's foot.

30. The device of claim 27 wherein each said exoskeleton foot further comprises an exoskeleton insole insertable inside said person's shoe to allow said exoskeleton foot to couple said person's foot.

31. The device of claim 1 wherein each said leg support further comprises an exoskeleton foot configured to be coupled to respective said person's foot and compliantly coupled to respective said shank link to allow the transfer of forces from said shank link to the ground.

32. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link and a shank link;
two knee joints, each configured to allow flexion and extension between respective shank link and respective thigh link; and
an exoskeleton trunk, configurable to be coupled to said person's upper body, rotatably connectable to said thigh links of said leg supports, the exoskeleton trunk including a connecting bracket configured to transfer weight of a load to said exoskeleton trunk and two hip links rotatably connected to said respective thigh links to allow for flexion and extension of said support legs relative to said exoskeleton trunk and rotatably connected to said connecting bracket via two hip abduction-adduction joints to allow for rotational motion of said leg supports about two abduction-adduction axes;
wherein the entire energy required for said flexion and extension between the shank link and the respective thigh link of a leg support over a cyclic knee motion is provided by said person.

33. The device of claim 32 wherein said abduction-adduction axes are generally parallel to each other.

34. The device of claim 32 wherein said hip abduction-adduction joints coincide on each other.

35. The device of claim 32 wherein said load is an object selected from a group consisting of a backpack, baby carrier, food containers, sacks, water jugs, tool boxes, barrels, ammunition, weaponry, bedding, first aid supplies, golf bags, mail bags, camera, leaf blower, compressor, electromechanical machineries and combinations thereof.

36. The device of claim 32 wherein said load is another person.

37. The device of claim 32 wherein said exoskeleton trunk further comprises hip abduction-adduction resilient elements configured to apply torques between said hip links and said connecting bracket.

38. The device of claim 37 wherein said hip abduction-adduction resilient elements, each comprise an elastic element or combination of elastic elements selected from a group consisting of extension spring, compression spring, leaf spring, air spring, gas spring, rubber, elastomer, surgical tube, and bungee cord.

39. The device of claim 32 wherein said connecting bracket further comprises an extension frame configured to hold said load in front of said person when said exoskeleton trunk is coupled to said person's upper body.

40. The device of claim 32 wherein said exoskeleton trunk comprises a human interface device capable of coupling said person's upper body to the lower extremity exoskeleton.

41. The device of claim 40 wherein said human interface device is capable of transferring a portion of a weight of said person to said exoskeleton trunk.

42. The device of claim 40 wherein said human interface device comprises an element or combination of elements selected from a group consisting of vests, belts, straps, shoulder straps, chest straps, body cast, harness, and waist belts.

43. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link, a shank link and a torque generator;
two knee joints, each configured to allow flexion and extension between respective shank link and respective thigh link, wherein each said torque generator is configured to allow flexion of said respective knee joint during swing phase, and to resist flexion of said respective knee joint during stance phase to allow the transfer of a force to ground; and
an exoskeleton trunk, configurable to be coupled to said person's upper body, rotatably connectable to said thigh links of said leg supports allowing for the flexion and extension between said leg supports and said exoskeleton trunk;
wherein the entire energy required for said flexion and extension between the shank link and the-respective thigh link of a leg support over a cyclic knee motion is provided by said person.

44. The device of claim 43 wherein said torque generators are hydraulic piston cylinders, wherein the hydraulic piston cylinder's resistive force can be controlled by controlling the fluid flow in a hydraulic valve.

45. The device of claim 43 wherein said torque generators are viscous rotary dampers, wherein the viscous rotary damper's resistive torque can be controlled by controlling the fluid flow in a hydraulic valve.

46. The device of claim 43 wherein said torque generators are hydraulic piston cylinders, wherein the hydraulic piston cylinder's impedance can be controlled by controlling a hydraulic valve.

47. The device of claim 43 wherein said torque generators are selected from a group consisting of friction brakes, viscosity based friction brakes, and Magnetorheological Fluid Devices.

48. The device of claim 43 further comprising a controller configured to control said torque generators.

49. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link, a shank link, and an exoskeleton foot configured to be coupled to respective said person's foot and rotatably coupled to respective said shank link to allow the transfer of forces from said shank link to the ground, wherein said exoskeleton foot rotates about an ankle plantar-dorsi flexion axis generally parallel to plantar-dorsi flexion axis in the human ankle;
two knee joints, each configured to allow flexion and extension between respective shank link and respective thigh link; and
an exoskeleton trunk, configurable to be coupled to said person's upper body, rotatably connectable to said thigh links of said leg supports allowing for the flexion and extension between said leg supports and said exoskeleton trunk;
wherein the entire energy required for said flexion and extension between the shank link and the respective thigh link of a leg support over a cyclic knee motion is provided by said person.

50. The device of claim 49 wherein each said leg support further comprises at least one ankle plantar-dorsi flexion resilient element resisting the rotation of respective said exoskeleton foot about said ankle plantar-dorsi flexion axis.

51. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link, a shank link and an exoskeleton foot configured to be coupled to respective said person's foot and rotatably coupled to respective said shank link to allow the transfer of forces from said shank link to the ground, wherein said exoskeleton foot rotates about an ankle abduction-adduction axis generally parallel to abduction-adduction axis in the human ankle;
two knee joints, each configured to allow flexion and extension between respective shank link and respective thigh link; and
an exoskeleton trunk, configurable to be coupled to said person's upper body, rotatably connectable to said thigh links of said leg supports allowing for the flexion and extension between said leg supports and said exoskeleton trunk;
wherein the entire energy required for said flexion and extension between the shank link and the respective thigh link of a leg support over a cyclic knee motion is provided by said person.

52. The device of claim 51 wherein said each leg support further comprises at least one ankle abduction-adduction resilient element to resist the rotation of respective said exoskeleton foot about said ankle abduction-adduction axis.

53. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link, a shank link and an exoskeleton foot configured to be coupled to respective said person's foot and rotatably coupled to respective said shank link to allow the transfer of forces from said shank link to the ground, wherein said exoskeleton foot rotates about an ankle rotation axis generally parallel to rotation axis in the human ankle;
two knee joints, each configured to allow flexion and extension between respective shank link and respective thigh link; and an exoskeleton trunk, configurable to be coupled to said person's upper body, rotatably connectable to said thigh links of said leg supports allowing for the flexion and extension between said leg supports and said exoskeleton trunk;

wherein the entire energy required for said flexion and extension between the shank link and the respective thigh link of a leg support over a cyclic knee motion is provided by said person.

54. The device of claim 53 wherein each said leg support further comprises at least one resilient element to resist the rotation of respective said exoskeleton foot about said ankle rotation axis.

55. A lower extremity exoskeleton, configurable to be coupled to a person, said lower extremity exoskeleton comprising:

two leg supports configurable to be coupled to said person's lower limbs and configured to rest on the ground during their stance phases where each said leg support comprises a thigh link and a shank link;

two knee joints, each configured to allow flexion and extension between respective shank link and respective thigh link;

an exoskeleton trunk configurable to be coupled to said person's upper body, rotatably connectable to said thigh links of said leg supports to allow for the flexion and extension between said leg supports and said exoskeleton trunk;

two torque generators capable of producing torque resisting flexion of said respective knee joint; and a controller configured to control said torque generators;

wherein the entire energy required for said flexion and extension between the shank link and the respective thigh link of a leg support over a cyclic knee motion is provided by said person.

56. The lower extremity exoskeleton of claim 55 wherein said controller increases the impedance of said torque generators to increase the resistance of said knee joints to flexion during a stance phase.

57. The lower extremity exoskeleton of claim 55 wherein said controller decreases the impedance of said torque generators to decrease the resistance of said knee joints to flexion during a swing phase.

58. The lower extremity exoskeleton of claim 55 further comprising at least one foot sensor per said leg support configured to produce a stance signal representing force on the bottom of each human foot; said controller configured to control the resistance to flexion in said exoskeleton knee joints as a function of said stance signals from said foot sensors.

59. The lower extremity exoskeleton of claim 55 further comprising at least one foot sensor per said leg support configured to produce a stance signal representing force on the bottom of each human foot; said controller configured to modulate the impedance of respective torque generator as a function of said stance signals from said foot sensors.

60. The lower extremity exoskeleton of claim 59 wherein each said leg support includes an exoskeleton foot connectable to respective said person's foot and connectable to respective said shank link to allow the transfer of forces from said shank link to the ground; wherein each said exoskeleton foot includes at least one foot sensor configured to produce a stance signal representing force on the bottom of respective human foot.

61. The device of claim 60 wherein said foot sensor is a pressure sensor configured to measure the pressure in a media trapped in a cavity in said exoskeleton foot.

62. The device of claim 59 wherein said foot sensor is located inside a human shoe.

63. The device of claim 59 wherein said foot sensor is located inside a human shoe sole.

64. The device of claim 59 wherein said foot sensor is connectable to the bottom of a human shoe.

65. The device of claim 55 wherein each said torque generators comprises a hydraulic piston-cylinder and said controller includes a hydraulic circuitry connectable to said hydraulic piston-cylinders; said hydraulic circuitry configured to modulate a hydraulic fluid flow to said hydraulic piston-cylinders.

66. The device of claim 55 wherein each said torque generator comprises a hydraulic piston and cylinder and said controller includes a hydraulic circuitry connectable to said hydraulic piston-cylinder; said hydraulic circuitry is configured to decrease a hydraulic fluid flow to said hydraulic-piston-cylinder during a stance phase.

67. The device of claim 55 wherein each said torque generator comprises a hydraulic piston-cylinder and said controller includes a hydraulic circuitry connectable to said hydraulic piston-cylinder; said hydraulic circuitry is configured to increase a hydraulic fluid flow to said hydraulic piston-cylinder during a swing phase.

68. The device of claim 55 wherein each said torque generator comprises a hydraulic piston-cylinder and said controller includes a hydraulic circuitry connectable to said hydraulic piston-cylinder; said hydraulic circuitry is configured to increase said knee joints' resistance to flexion during a stance phase.

69. The device of claim 55 wherein each said torque generator comprises a hydraulic piston-cylinder and said controller includes a hydraulic circuitry connectable to said hydraulic piston-cylinder; said hydraulic circuitry is configured to decrease said knee joints' resistance to flexion during a swing phase.

70. The device of claim 59 wherein each said torque generator comprises a hydraulic piston-cylinder and said controller includes a hydraulic circuitry connectable to said hydraulic piston and cylinder; said controller is configured to control said hydraulic circuitry as a function of said stance signal.

71. The device of claim 59 wherein each said torque generator comprises a hydraulic piston-cylinder and said controller includes a hydraulic circuitry connectable to said hydraulic piston-cylinder; said controller is configured to decrease a hydraulic fluid flow to said hydraulic piston cylinder when said stance signal detects a force on the bottom of the human foot.

72. The device of claim 59 wherein each said torque generator comprises a hydraulic piston-cylinder and said controller includes a hydraulic circuitry connectable to said hydraulic piston-cylinder; said controller is configured to increase the impedance of said hydraulic piston-cylinder when said stance signal detects a force on the bottom of the human foot.

73. The device of claim 59 wherein each said torque generator comprises a hydraulic piston and cylinder and said controller includes a hydraulic circuitry connectable to said hydraulic piston-cylinder; said controller is configured to increase the resistance of said knee joint to flexion when said stance signal represents a force on the bottom of the human foot.

74. The device of claim 65 wherein said hydraulic circuitry comprises an actuated flow restricting valve connecting said hydraulic piston-cylinder to a hydraulic reservoir; said actuated flow restricting valve is configured to restrict the hydraulic fluid flow during a stance phase and allow for minimum resistance hydraulic fluid flow during a swing phase.

75. The device of claim 65 wherein said hydraulic circuitry includes a hydraulic three-way valve connecting said hydraulic piston-cylinder to a hydraulic reservoir either through a needle valve or a bypass line; said hydraulic three-way valve is configured to connect said hydraulic piston-cylinder to said hydraulic reservoir through said needle valve during a stance phase and connect said hydraulic piston-cylinder to said hydraulic reservoir through said bypass line during a swing phase.

76. The device of claim 65 wherein said hydraulic circuitry includes a hydraulic three-way valve connecting said hydraulic piston-cylinder to a hydraulic reservoir either through a needle valve, a bypass line or a check valve; said hydraulic three-way valve is configured to connect said hydraulic piston-cylinder to said hydraulic reservoir through said needle valve during a stance phase and connect said hydraulic piston-cylinder to said hydraulic reservoir through said bypass line during a swing phase.

77. The device of claim 65 wherein said hydraulic circuitry comprises an actuated flow restricting valve and a check valve connecting said hydraulic piston-cylinder to a hydraulic reservoir; said actuated flow restricting valve configured to restrict the hydraulic fluid flow during a stance phase and to allow for minimum resistance hydraulic fluid flow during a swing phase.

78. The device of claim 65 wherein said hydraulic circuitry comprises a two-way valve capable of selecting between a set orifice size or fully open, and a check valve connecting said hydraulic piston-cylinder to a hydraulic reservoir; said two-way valve configured to restrict the hydraulic fluid flow during a stance phase and allow for minimum resistance hydraulic fluid flow during a swing phase.

79. The device of claim 65 wherein said hydraulic circuitry comprises a two-way valve, a check valve, and a needle valve connecting said hydraulic piston-cylinder to a hydraulic reservoir; said two-way valve configured to allow for minimum resistance hydraulic fluid flow during a swing phase and direct the hydraulic fluid flow through the needle valve during a stance phase.

80. A method of carrying an object using a lower extremity exoskeleton, said lower extremity exoskeleton coupled to said object and having:
two leg supports configured to rest on the ground during their stance phases where each said leg support comprises a thigh link and a shank link;
two knee joints, each configured to allow flexion and extension between respective shank link and respective thigh link; and
an exoskeleton trunk, rotatably connectable to said thigh links of said leg supports allowing for the flexion and extension between said leg supports and said exoskeleton trunk;
two torque generators; and
a controller configured to control said torque generators
said method comprising:
coupling a person's leg to one of said two leg supports;
coupling a person's upper body to said exoskeleton trunk; and
controlling said torque generators to allow the flexion of said respective knee joints during swing phase, and to resist flexion of said respective knee joints during stance phase to allow the transfer of a force to ground;
wherein the entire energy required for said flexion and extension between the shank link and the respective thigh link of a leg support over a cyclic knee motion is provided by said person.

81. The method of claim 80 wherein said exoskeleton further includes at least one foot sensor per said leg support which transmits a stance signal representing the force on the bottom of the feet of said person to said controller.

82. A lower extremity exoskeleton, configurable to be coupled to a person, said lower extremity exoskeleton comprising:
two leg supports configurable to be coupled to said person's lower limbs and configured to rest on the ground during their stance phases where each said leg support comprises a thigh link, a shank link, and an exoskeleton foot;
two knee joints, each configured to allow flexion and extension between respective shank link and respective thigh link;
an exoskeleton trunk, configurable to be coupled to said person's upper body, rotatably connectable to said thigh links of said leg supports to allow for the flexion and extension between said leg supports and said hip mechanism;
at least one foot sensor per said leg support which produces a stance signal representing force on the bottom of the feet of said human;
two torque generators each configured to allow flexion of said respective knee joint during swing phase, and to resist flexion of said respective knee joint during stance phase to allow the transfer of a force to ground; and
a controller configured to control said torque generators wherein the entire energy required for said flexion and extension between the shank link and the respective thigh link of a leg support over a cyclic knee motion is provided by said person.

83. The device of claim 82, wherein each said leg support further comprises at least one knee resilient element configured to encourage flexion of said respective knee joint.

84. The device of claim 82, wherein each said leg support further comprises at least one knee resilient element configured to encourage extension of said respective knee joint.

* * * * *